US011884686B2

(12) United States Patent
Meijer et al.

(10) Patent No.: US 11,884,686 B2
(45) Date of Patent: Jan. 30, 2024

(54) CHELATE COMPOUNDS

(71) Applicant: GE HEALTHCARE AS, Oslo (NO)

(72) Inventors: Andreas Richard Meijer, Oslo (NO); Mikkel Jacob Thaning, Oslo (NO); Brian Christopher Bales, Niskayuna, NY (US); Michael James Rishel, Niskayuna, NY (US)

(73) Assignee: GE HEALTHCARE AS, Oslo (NO)

( * ) Notice: Subject to any disclaimer, the term of this patent is extended or adjusted under 35 U.S.C. 154(b) by 1120 days.

(21) Appl. No.: 16/311,564

(22) PCT Filed: Jun. 20, 2017

(86) PCT No.: PCT/EP2017/065135
§ 371 (c)(1),
(2) Date: Dec. 19, 2018

(87) PCT Pub. No.: WO2017/220610
PCT Pub. Date: Dec. 28, 2017

(65) Prior Publication Data
US 2019/0233450 A1    Aug. 1, 2019

(30) Foreign Application Priority Data
Jun. 20, 2016 (GB) ..................... 1610738

(51) Int. Cl.
C07F 13/00 (2006.01)
C07D 471/08 (2006.01)

(52) U.S. Cl.
CPC .......... C07F 13/005 (2013.01); C07D 471/08 (2013.01)

(58) Field of Classification Search
None
See application file for complete search history.

(56) References Cited

U.S. PATENT DOCUMENTS

| | | |
|---|---|---|
| 5,215,680 A | 6/1993 | D'Arrigo |
| 5,334,371 A | 8/1994 | Gries et al. |
| 5,428,139 A | 6/1995 | Kiefer et al. |
| 5,876,695 A | 3/1999 | Gries et al. |
| 6,440,956 B1 | 8/2002 | Port |
| 7,988,950 B2 | 8/2011 | Aime et al. |
| 8,114,863 B2 * | 2/2012 | Port ................... A61K 51/0402 514/183 |
| 8,192,721 B2 | 6/2012 | Rowe |
| 9,486,544 B2 | 11/2016 | Meijer |
| 10,494,379 B2 | 12/2019 | Botár et al. |
| 10,730,897 B2 | 8/2020 | Thaning et al. |
| 10,781,188 B2 | 9/2020 | Lattuada et al. |
| 11,110,185 B2 | 9/2021 | Meijer et al. |
| 11,110,186 B2 | 9/2021 | Bales et al. |
| 2006/0239913 A1 | 10/2006 | Port et al. |
| 2006/0239926 A1 * | 10/2006 | Port ................... C07K 5/1005 424/9.363 |
| 2007/0098643 A1 | 5/2007 | Nachman et al. |
| 2008/0305049 A1 | 12/2008 | Degani et al. |
| 2009/0169479 A1 * | 7/2009 | Port ................... A61K 51/0478 540/472 |
| 2009/0297008 A1 | 12/2009 | Taxt et al. |
| 2012/0244081 A1 * | 9/2012 | Meijer ................. A61K 49/106 540/472 |
| 2016/0045623 A1 | 2/2016 | Kaufman et al. |
| 2016/0101196 A1 | 4/2016 | Medina et al. |
| 2022/0315616 A1 | 10/2022 | Bales et al. |

FOREIGN PATENT DOCUMENTS

| | | |
|---|---|---|
| CN | 101305006 A | 11/2008 |
| CN | 102639152 A | 8/2012 |
| CN | 103224495 A | 7/2013 |
| CN | 105142649 A | 12/2015 |
| EP | 0258616 A1 | 3/1988 |
| EP | 391766 A1 | 10/1990 |
| EP | 0352218 A3 | 1/1991 |
| EP | 0463644 A2 | 1/1992 |
| EP | 1931673 A1 | 6/2008 |
| EP | 2457914 A1 | 5/2012 |
| EP | 1931673 B1 | 8/2012 |
| EP | 2988756 A1 | 3/2016 |
| RU | 2114115 C1 | 6/1998 |
| RU | 2232763 C2 | 7/2004 |
| WO | WO-1990/003804 A1 | 4/1990 |
| WO | WO-1991010645 A2 | 7/1991 |
| WO | 9311801 A1 | 6/1993 |
| WO | WO-1993011800 A1 | 6/1993 |
| WO | WO-1993011802 A1 | 6/1993 |
| WO | 9426313 A1 | 11/1994 |
| WO | WO-1994026754 A1 | 11/1994 |
| WO | 03074523 A1 | 9/2003 |
| WO | 2004112839 A1 | 12/2004 |
| WO | 2006080022 A2 | 8/2006 |
| WO | 2007042506 A1 | 4/2007 |
| WO | WO-2009103744 A2 | 8/2009 |
| WO | 2011073371 A1 | 6/2011 |
| WO | 2017220610 A1 | 12/2017 |
| WO | WO-2018115314 A1 | 6/2018 |

OTHER PUBLICATIONS

Wooten, A.L., et al., "Cross-sections for (p,x) reactions on natural chromium for the production of 52,52m,54Mn radioisotopes", Appl. Rad. Iso., pp. 154-161 (Year: 2015).*
Office Action received in Russian Application No. 2018145061/04 dated Apr. 12, 2021, with translation, 2021 20 pages.
Chinese Office Action received in Application No. 201780051082.4 dated Dec. 23, 2020, 11 pages.
Chinese Search Report received in Application No. 201780051082.4 dated Dec. 16, 2020.
International Search Report corresponding to Application No. PCT/EP2017/065135, dated Sep. 8, 2017.
Great Britain Search Report corresponding to British Application No. GB1610738.5, dated Apr. 10, 2017.

(Continued)

Primary Examiner — Michael G. Hartley
Assistant Examiner — Lance W Rider
(74) Attorney, Agent, or Firm — Goodwin Procter LLP

(57) ABSTRACT

The invention provides compounds suitable for use as contrast agents in magnetic resonance imaging (MRI). The compounds of the present invention are manganese (II) complexes having advantageous properties as compared with similar known compounds.

6 Claims, 11 Drawing Sheets

(56) References Cited

OTHER PUBLICATIONS

Russian Office Action Received in Application No. 2018145061.04 dated Jul. 28, 2020, 11 pages. (with translations).
Russian Search Report Received in Application No. 2018145061.04 dated Jul. 27, 2020, 4 pages. (with translations).
Office Action received in Chinese Application No. 202010082357.4 dated Feb. 7, 2022, with translation, 16 pages.
Aime, S. et al., "[GdPCP2A(H2O)2]-: A paramagnetic contrast agent designed for improved applications in magnetic resonance imaging," J. Med. Chem. 2000, vol. 43, No. 21, pp. 4017-4024.
International Search Report and Written Opinion corresponding to International Appl. No. PCT/EP2010/070029, dated Apr. 12, 2011. 8 pages.
Aime, S. et al., "Mannich Reaction as a New Route to Pyridine-Based Polyaminocarboxylic Ligands, "Org. Lett. 2003, vol. 6. No. 8, pp. 1201-1204.
European notice of allowance corresponding to EP Appl. No. 17822298.0 dated Dec. 3, 2019.
International Search Report and Written Opinion corresponding to International Application No. PCT/EP2017/084148, dated Mar. 22, 2018, 12 pages.
Wen, Jinghan, et al., "A mononuclear Mn2+ complex based on a novel tris-(ethyl acetate) pendant-armed etraazamacrocycle: Effect of pyridine on self-assembly and weak interactions," Inorg. Chem. Comm. 2012, vol. 21, pp. 16-20.
Pan, Dipanjan, et al., "Manganese-based MRI contrast agents: past, present, and future," Tetrahedron, 2011, vol. 67, No. 14, pp. 8431-8444.
Gale, Eric M., et al., "A Manganese Alternative to Gadolinium for MRI Contrast," J. Am. Chem. Soc. 2015, vol. 137. No. 49, pp. 15548-57.
Drahos, et al., "Manganese (II) Complexes as Potential Contrast Agents for MRI," EurJIC, European Journal of Inorganic Chemistry, Microreview, 2012, pp. 1975-1986.
Henig, et al., "Macrocyclic Gd3+ Chelates Attached to a Silsesquioxane Core as Potential Magnetic Resonance Imaging Contrast Agents: Synthesis, Physicochemical Characterization, and Stability Studies," Inorganic Chemistry Miele, 2010, vol. 49, pp. 6124-6138.
Kubicek, et al., "Design and Function of Metal Complexes as Contrast Agents in MRI," Centre de Biophysique Moleculaire, France, Advance in Inorganic Chemistry, 2009, vol. 61, 67 pages.
Sieber, et al. "Gadolinium-Based Contrast Agents and Their Potential Role in the Parthenogenesis of Nephrogenic Systemic Fibrosis: The Role of Excess Ligand," Journal of magnetic Resonance Imaging, 2008, vol. 27, pp. 955-962.
International Search Report and the Written Opinion corresponding to International Appl. No. PCT/EP2018/086426, dated Mar. 15, 2019, 7 pages.
Botta, et al., "Mn{II} compounds as an alternative to Gd-based MRI probes," Future Medicinal Chemistry, 2019, vol. 11, No. 12, pp. 1461-1483.
Garda, et al., "Effect of the Nature of Donor Atoms on the Thermodynamic, Kinetic and Relaxation Properties of Mn(II): Complexes Formed with Some Trisubstituted 12-Membered Macrocyclic Ligands," Frontiers in Chemistry, 2018, vol. 6, Article 232, 14 pages.
International Search Report and Written Opinion corresponding to International Application No. PCT/EP2020/074645 dated Nov. 30, 2020, 9 pages.
Garda, et al., "Physico-chemical properties of MnII complexes formed with cis- and trans-DO2A: thermodynamic, electrochemical and kinetic studies," J. Inorg. Biochem. 2016, vol. 163, pp. 206-213.
FDA, "FDA Drug Safety Communication: FDA wans that gadolinium-based contrast agents (GBCAs) are retained in the body; requires new class warnings," retrieved on the FDA website May 26, 2023, 5 pages.
Hovland, R. et al., Preparation and in vitro evaluation of novel amphiphilic GdPCTA-[12] derivative; a micellar MRI contrast agent. Org. Biomol. Chem. 2003, vol. 1, p. 644-647.
Levy et al., "Development of a Multigram Asymmetric Synthesis of 2-(R)-2-(4,7,10-Tris tert-Butylcarboxymethyl-1,4,7,10-tetraazacyclododec-1-yl)-pentanedioic Acid, 1-tert-Butyl Ester, (R)-tert-Bu4-DOTAGA (1)" Org. Process Res. Dev. 2009, 13(3) 535-542.

\* cited by examiner

CHELATE COMPOUNDS

This application is a filing under 35 U.S.C § 371 and claims priority to international patent application number PCT/EP2017/065135, filed Jun. 20, 2017, published Dec. 28, 2017, as WO 2017/220610, which claims priority to patent application number 1610738.5 filed in Great Britain on Jun. 20, 2016.

TECHNICAL FIELD OF THE INVENTION

The invention relates to chelate compounds and their use as contrast agents in magnetic resonance imaging (MRI) procedures.

DESCRIPTION OF RELATED ART

MRI is a medical imaging technique in which areas of the body are visualised via the nuclei of selected atoms, especially hydrogen nuclei. The MRI signal depends upon the environment surrounding the visualised nuclei and their longitudinal and transverse relaxation times, T1 and T2. Thus, in the case when the visualised nucleus is a proton, the MRI signal intensity will depend upon factors such as proton density and the chemical environment of the protons. Contrast agents can be used in MRI to improve the imaging contrast. They work by effecting the T1, T2 and/or T2* relaxation time and thereby influence the contrast in the images.

It is known that the T1, T2 and/or T2* relaxation times can be optimized for a chelated paramagnetic contrast agents by structural modification. Of particular importance is the presence and residence time of a water molecule bound to the paramagnetic ion and the rotational correlation time of the contrast agent. The presence and residence time of a water molecule, bound to the paramagnetic ion, can be modulated by the choice of paramagnetic ion and the chelating moiety. The rotational correlation time can be modulated by varying the size of the contrast agent.

Several types of contrast agents are known for use in MRI. Blood pool MR contrast agents, for instance superparamagnetic iron oxide particles, are retained within the vasculature for a prolonged time. They have proven extremely useful to enhance contrast e.g. in the liver but also to detect capillary permeability abnormalities such as "leaky" capillary walls in tumours which are a result of tumour angiogenesis.

The solubility of the paramagnetic chelate in water is also an important factor when they are used as contrast agents for MRI because they are administered to patients in relatively large doses. A highly water-soluble paramagnetic chelate requires a lower injection volume, is thus easier to administer to a patient and causes less discomfort. Water-soluble paramagnetic chelates, i.e. complexes of a chelator and a paramagnetic metal ion are well known—for instance the commercially-available gadolinium chelates Omniscan™ (GE Healthcare), Dotarem™ (Guerbet), Gadavist™ (Bayer) and Magnevist™ (Bayer). Because of their low molecular weight they rapidly distribute into the extracellular space (i.e. the blood and the interstitium) when administered into the vasculature. They are also cleared relatively rapidly from the body.

Several publications describe work carried out with the goal of developing improved paramagnetic chelate compounds. For example, U.S. Pat. No. 8,540,966 teaches the following generalised structure:

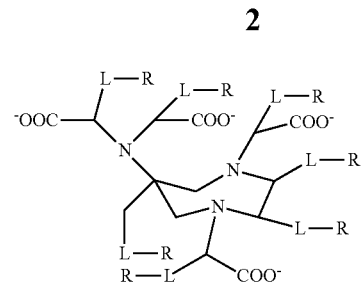

Where L is a linker and R is H or a $C_{2-70}$ aminopolyol moiety. The experimental examples of U.S. Pat. No. 8,540,966 compare certain of these compounds with commercially-available gadolinium chelates to demonstrate a similar pharmacokinetic profile but with higher relaxivity.

EP1931673 teaches the following generalised structure:

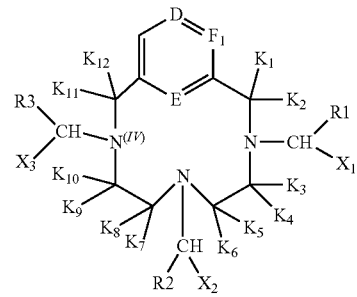

Each R in the above structure is defined in EP1931673 as a co-ordinating ligand and each X comprises at least one $C_{1-6}$ hydroxyalkyl group. EP1931673 emphasises the relaxivity properties of the compounds. EP1931673 notes that the compounds may be complexed with a paramagnetic metal ion selected from $Gd^{3+}$, $Mn^{2+}$ and $Fe^{3+}$ but in reality the focus is on chelate structures that are suitable for stable complexation of $Gd^{3+}$ e.g. the following gadolinium-containing complex:

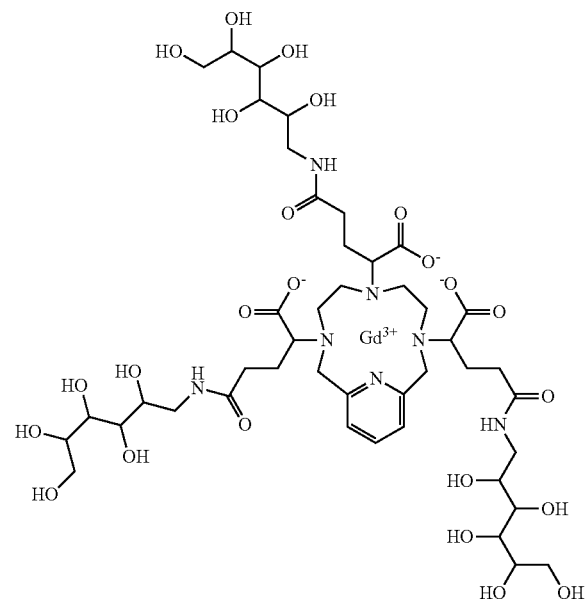

All disclosed complexes are heptadentate, as four nitrogens and three carboxylic acid groups are coordinating to the complexated metal ion. The detrimental effect of heptadentate manganese chelates has been described in WO2011073371.

A key property of MRI chelate compounds is for the paramagnetic ion to be retained as far as possible within the chelate structure. Paramagnetic ion released from the chelate in vivo can interfere with biological pathways and potentially induce toxicity. The ability of a chelate to retain the paramagnetic ion (also referred to herein as stability) is also a property that can be modulated by structural design of the cheland moiety. Of particular interest is the kinetic stability, measured as a dissociation half-life, which indicates the degree of inertia towards altered chemical surroundings (i.e. endogenous ions). The above-cited publications do not discuss transmetallation inertness of the compounds they describe.

As can be appreciated from the commercially-available agents and the focus of the prior art, gadolinium is the most widely used paramagnetic metal ion for MRI chelates, which is down to its favourable relaxivity properties. Stability of the paramagnetic ion within the chelate structure is particularly important for gadolinium chelates as there are well-known issues connected with free gadolinium and toxicity. Because of these issues, there is a motivation to seek alternatives to gadolinium.

The manganese(II) ion is a paramagnetic species with a high spin number and a long electronic relaxation time and the potential of a manganese(II) based high relaxivity contrast agent has been reported in the literature (Tóth, É; Advances in Inorganic Chemistry, 2009, 61(09), 63-129). Certain manganese(II) chelates developed to date have however proved to be much less stable compared to corresponding gadolinium chelates. For example, the manganese chelate of DOTA (MnDOTA) is several hundred times less stable compared to the corresponding gadolinium complex (GdDOTA (DrahõS, B; Inorganic Chemistry, 2012(12), 1975-1986).

The work described in WO2011073371 demonstrates a molecular design that favours high chelate stability and a high relaxivity. This makes these compounds very suitable for use as MRI contrast agents. An exemplary compound of WO2011073371 has the following structure (also referred to herein as "prior art Mn Chelate"):

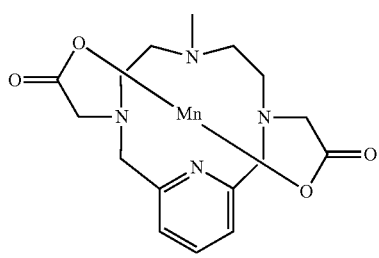

Nevertheless, there is still scope for further manganese chelate compounds having improved and sustained kinetic stability while maintaining viable relaxation properties.

SUMMARY OF THE INVENTION

In one aspect the present invention provides a compound of Formula I:

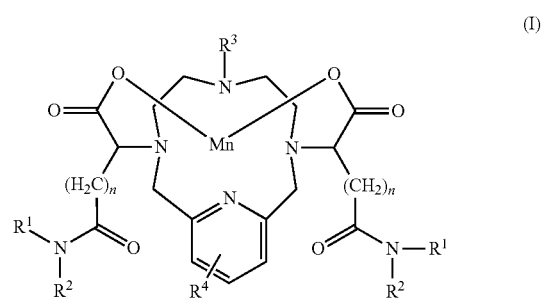

or a salt or solvate thereof, wherein:

each $R^1$ is independently selected from the group comprising $C_{1-20}$ hydroxyalkyl, $C_{1-6}$ alkyl, $C_{3-6}$ aryl optionally-substituted with one or more substituents selected from halo and —C(=O)—NH—$C_{1-6}$ hydroxyalkyl, or a carbohydrate moiety;

each $R^2$ is independently selected from the group comprising $C_{1-20}$ hydroxyalkyl, $C_{1-6}$ alkyl or hydrogen;

$R^3$ is selected from the group comprising $C_{1-3}$ alkyl or —(CH$_2$)$_m$—C(=O)—NR$^5$R$^6$ wherein m is an integer from 2-5, and $R^5$ and $R^6$ are as respectively defined for $R^1$ and $R^2$;

$R^4$ represents 0-3 substituents selected from the group comprising hydroxy, $C_{1-6}$ alkyl and $C_{1-6}$ hydroxyalkyl; and, each n is an integer from 0-4;

and wherein the compound of Formula I comprises at least two hydroxy groups.

In another aspect, the present invention provides a method for the preparation of a compound of Formula I of the invention comprising:

activating the carboxylate groups of a compound of Formula II with a peptide reagent

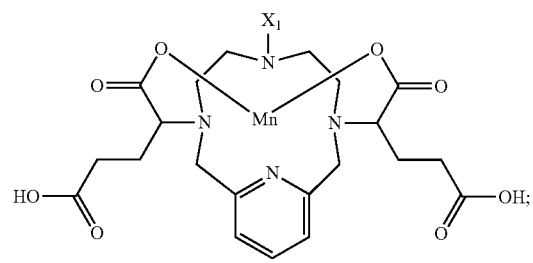

then, (ii) coupling said activated compound of Formula II with an amine derivative of substituent —NR$^1$R$^2$ to arrive at said compound of Formula I wherein $R^1$ and $R^2$ are as defined in Claim 1.

In another aspect, the present invention provides a method for the preparation of a compound of Formula II as defined herein comprising alkylation of a compound of Formula III:

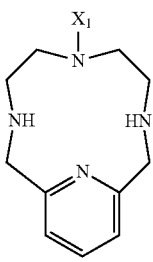

(III)

wherein $X_1$ is methyl or —$(CH_2)_3$—COOH.

In another aspect, the present invention provides a pharmaceutical composition comprising the compound of Formula I of the invention together with a biocompatible carrier in a form suitable for mammalian administration.

In another aspect, the present invention provides a method comprising:
(i) administration to a subject of the compound of Formula I of the invention or the pharmaceutical composition of the invention;
(ii) detection of magnetic resonance (MR) signals from said subject or parts of said subject in which said compound has distributed;
(iii) generation of MR images and/or MR spectra from said detected signals.

The compounds of the present invention have been demonstrated to possess properties that indicate their usefulness as MRI contrast agents.

The solubility of compounds of the invention measured as described in Example 13 demonstrated their suitability for use as contrast agents for MRI.

In vitro relaxivity measurements to evaluate the efficiency of compounds of the invention (see Example 14) demonstrated that these compounds induce an increase of both the longitudinal and transverse relaxation rates (e.g., $1/T_1$ and $1/T_2$ respectively) of the water molecules coordinated with the metal ion.

Experiments to test the kinetic inertness of compounds of the invention was evaluated in the presence of competing metal ions $Cu^{2+}$ and $Zn^{2+}$ in slightly acidic solution (see Example 15). These experiments demonstrated that compounds of the present invention have favourable characteristics compared with the prior art.

Compounds of the invention showed an improvement in the kinetic inertness of the Mn(II) based chelates with a slower dissociation compared to a prior art compound.

In summary therefore, the compounds of the present invention demonstrate an advantageous balance between contrast agent efficiency and improved stability in vivo not previously demonstrated Mn(II) chelate compounds. The additional in vivo stability indicates that the compounds of the invention could be an attractive alternative to Gd(III) in the future generation of clinical contrast agents for medical MRI.

DETAILED DESCRIPTION OF THE PREFERRED EMBODIMENTS

Figure 1:
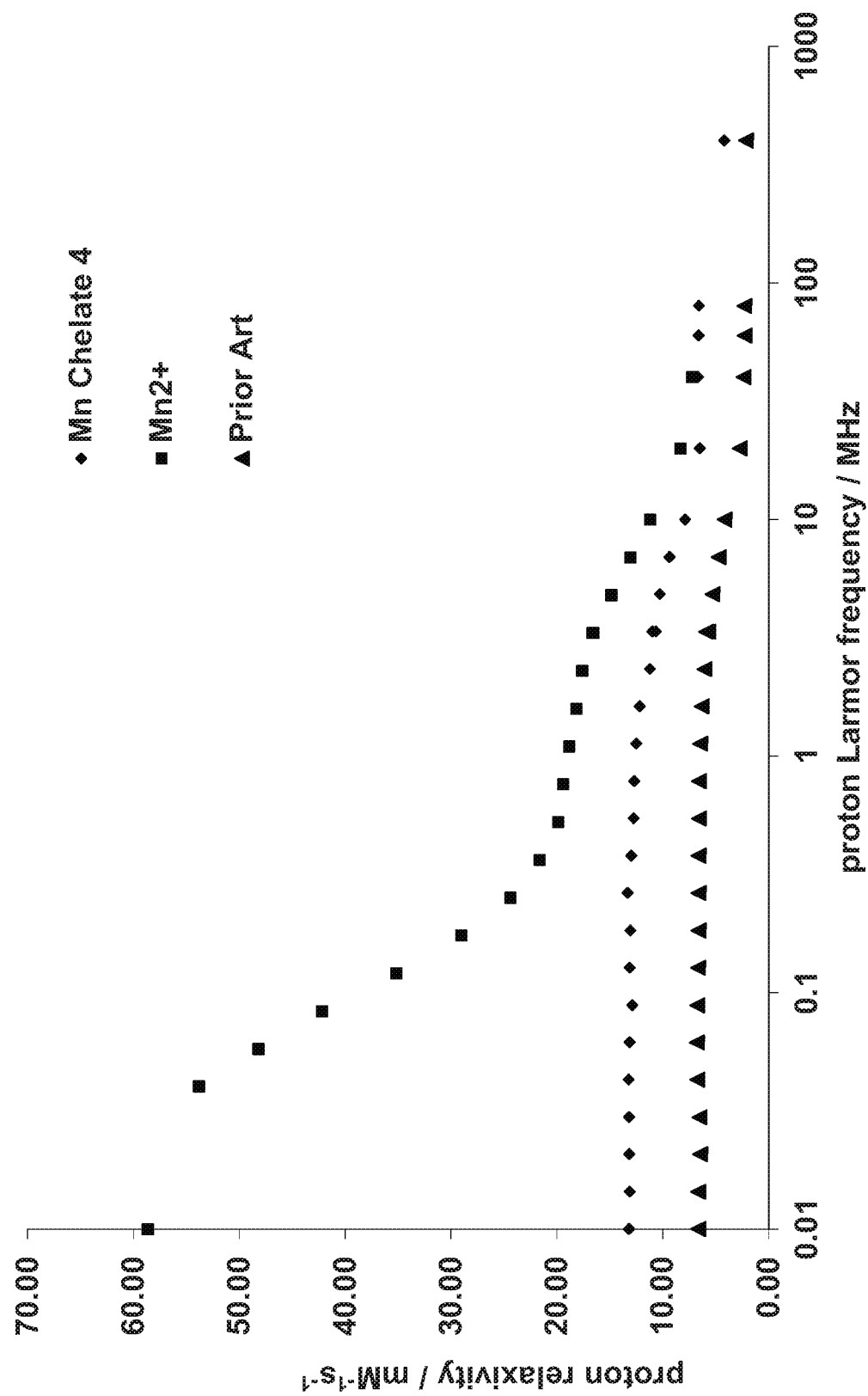
FIG. 1 illustrates the dissociation kinetics of Mn(II) based chelates as tested in the methods of Example 15.

To more clearly and concisely describe and point out the subject matter of the claimed invention, definitions and exemplary embodiments are provided hereinbelow for specific terms used throughout the present specification and claims. Any exemplification of specific terms herein should be considered as a non-limiting example.

The terms "comprising" or "comprises" have their conventional meaning throughout this application and imply that the agent or composition must have the essential features or components listed, but that others may be present in addition. The term 'comprising' includes as a preferred subset "consisting essentially of" which means that the composition has the components listed without other features or components being present.

The term "alkyl", alone or in combination, means a straight-chain or branched-chain alkyl radical having the general formula $C_nH_{2n+1}$. Examples of such radicals include methyl, ethyl, and isopropyl.

The term "hydroxyl" refers to the group —OH.

The term "hydroxyalkyl" refers to an alkyl group as defined above comprising a hydroxyl substituent as defined above.

The term "aryl" refers to a functional group or substituent derived from an aromatic ring, usually an aromatic hydrocarbon, examples of which include phenyl and pyridyl. In one embodiment aryl groups of the present invention are aromatic 6-membered rings with between 0-3 heteroatoms selected from O, N and S.

The term "halogen" or "halo" means a substituent selected from fluorine, chlorine, bromine or iodine.

The term "carbohydrate moiety" refers to an aldehyde or a ketone derivative of a polyhydric alcohol and includes monosaccharide, disaccharide and oligosaccharide residues. Non-limiting examples include fructose, glucose and sucrose residues.

In one embodiment of said compound of Formula I each $R^1$ is $C_{1-12}$ hydroxyalkyl.

In one embodiment of said compound of Formula I each $R^1$ is $C_{3-6}$ hydroxyalkyl.

In one embodiment of said compound of Formula I each $R^1$ is $C_6$ hydroxyalkyl.

In one embodiment of said compound of Formula I each $R^1$ is independently selected from the group comprising:

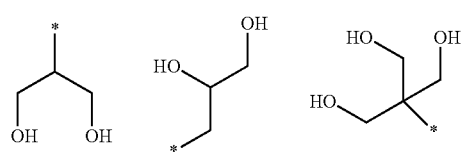

-continued

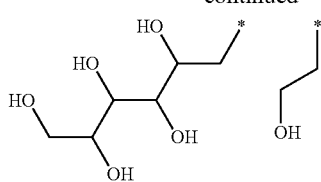

wherein in each case the asterisk denotes the point of attachment to the rest of the compound of Formula I.

In one embodiment of said compound of Formula I each $R^1$ is independently selected from the group comprising:

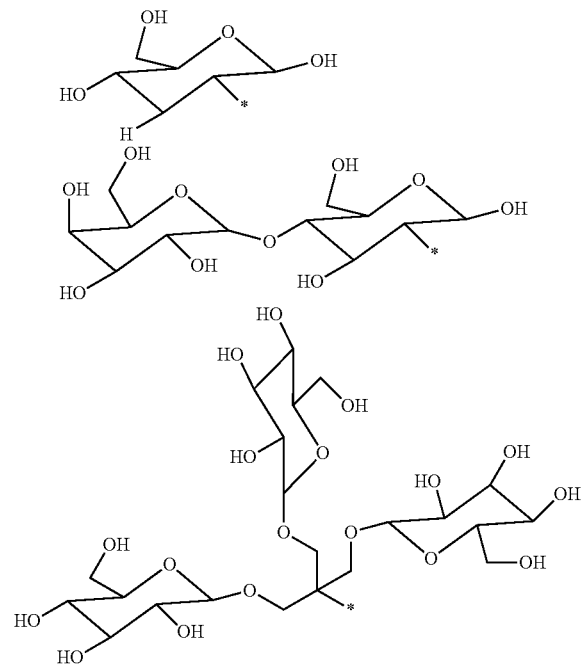

wherein in each case the asterisk denotes the point of attachment to the rest of the compound of Formula I.

In one embodiment of said compound of Formula I each $R^1$ is a $C_{3-6}$ aryl substituted with one or more substituents selected from halo and —C(=O)—NH—$C_{1-6}$ hydroxyalkyl.

In one embodiment of said compound of Formula I said $C_{3-6}$ aryl is phenyl.

In one embodiment of said compound of Formula I said halo is iodo.

In one embodiment of said compound of Formula I —C(=O)—NH—$C_{1-6}$ hydroxyalkyl is —C(=O)—NH—$CH_2$—C(OH)—$CH_2$—C(OH).

In one embodiment of said compound of Formula I each $R^1$ is:

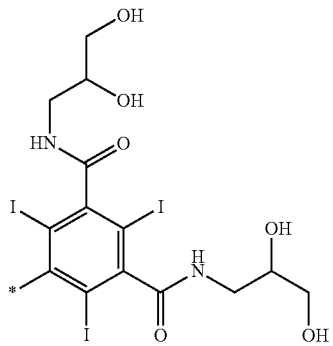 [SMILES: *c1c(I)c(C(=O)NCC(O)CO)c(I)c(C(=O)NCC(O)CO)c1I]

wherein the asterisk denotes the point of attachment to the rest of the compound of Formula I.

In one embodiment of said compound of Formula I each $R^1$ is:

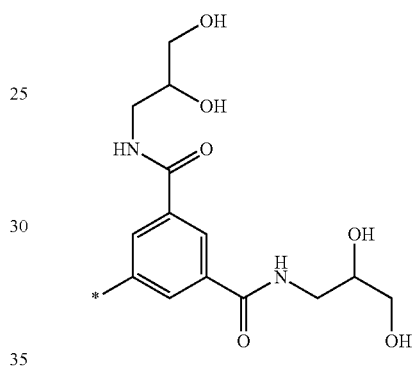

wherein the asterisk denotes the point of attachment to the rest of the compound of Formula I.

In one embodiment of said compound of Formula I each $R^1$ is the same.

In one embodiment of said compound of Formula I each $R^2$ is $C_{1-3}$ alkyl.

In one embodiment of said compound of Formula I each $R^2$ is methyl.

In one embodiment of said compound of Formula I each $R^2$ is hydrogen.

In one embodiment of said compound of Formula I each $R^2$ is $C_{1-20}$ hydroxyalkyl.

In one embodiment of said compound of Formula I each $R^2$ is $C_{1-6}$ hydroxyalkyl. When each $R^2$ is $C_{1-6}$ hydroxyalkyl, in one embodiment each $R^1$ is also $C_{1-6}$ hydroxyalkyl, and in another embodiment $R^2$ and $R^1$ are the same.

In one embodiment of said compound of Formula I each $R^2$ is the same.

In one embodiment of said compound of Formula I each n is an integer from 1-3.

In one embodiment of said compound of Formula I n is 1.
In one embodiment of said compound of Formula I n is 2.
In one embodiment of said compound of Formula I each n is 3.
In one embodiment of said compound of Formula I $R^3$ is $C_{1-3}$ alkyl.
In one embodiment of said compound of Formula I $R^3$ is methyl.
In one embodiment of said compound of Formula I $R^3$ is —$(CH_2)_m$—C(=O)—$NR^5R^6$ as defined herein.

In one embodiment of said compound of Formula I $R^5$ is as defined for $R^1$ herein.

In one embodiment of said compound of Formula I $R^6$ is as defined for $R^2$ herein.

In one embodiment of said compound of Formula I m is 3.

In one embodiment of said compound of Formula I n is 2.

In one embodiment of said compound of Formula I $R^4$ represents 0 substituents.

In one embodiment of said compound of Formula I $R^4$ represents 1 or 2 hydroxy groups.

In one embodiment of said compound of Formula I $R^4$ represents 2 hydroxy groups at the meta positions of the pyridyl ring.

In one embodiment said compound of Formula I comprises at least 4 hydroxy groups.

In one embodiment said compound of Formula I comprises 4-15 hydroxy groups.

In one embodiment said compound of Formula I comprises 5-10 hydroxy groups.

In one embodiment of the compound of the invention said Mn is an enriched isotope of Mn selected from the group comprising $^{52}$Mn and $^{54}$Mn. In one embodiment said Mn isotope is $^{54}$Mn.

Non-limiting examples of compounds of Formula I are the following compounds:

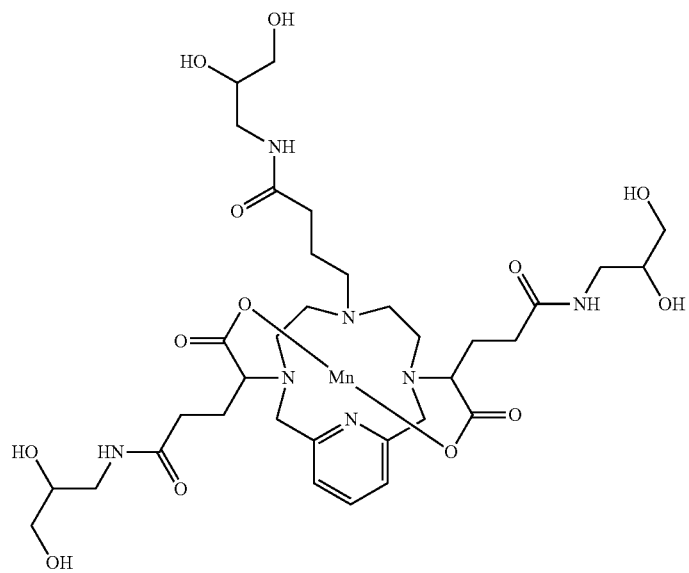

Mn Chelate 1 Racemate

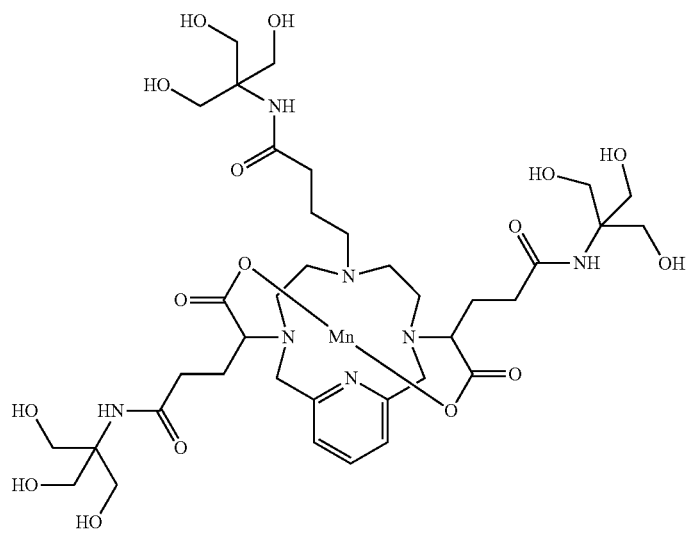

Mn Chelate 2 Racemate

-continued
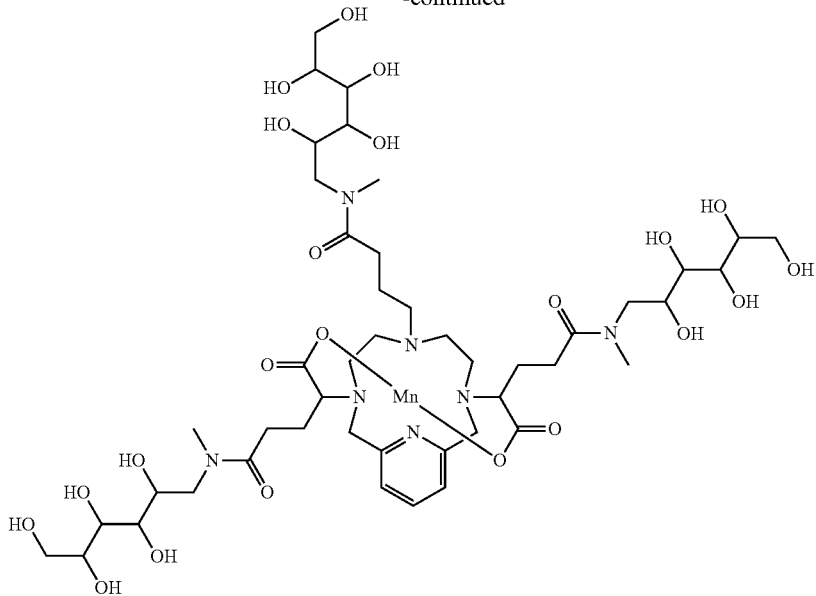
Mn Chelate 3 Racemate
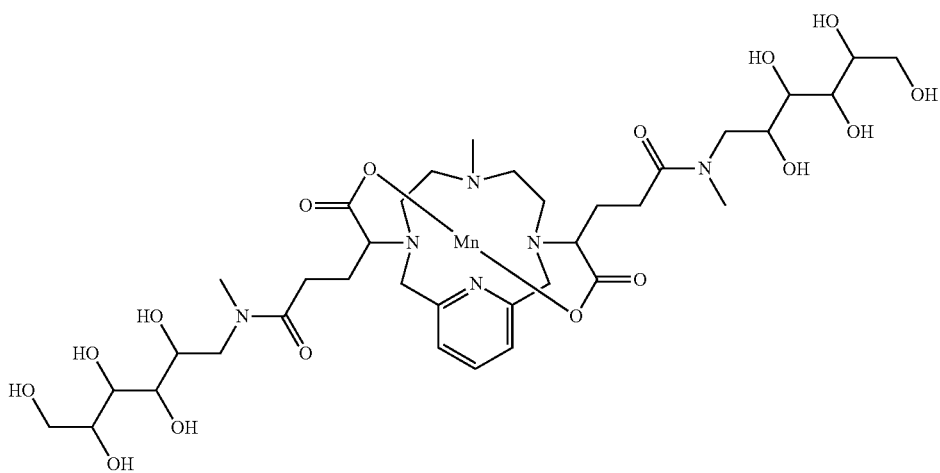
Mn Chelate 4 Racemate
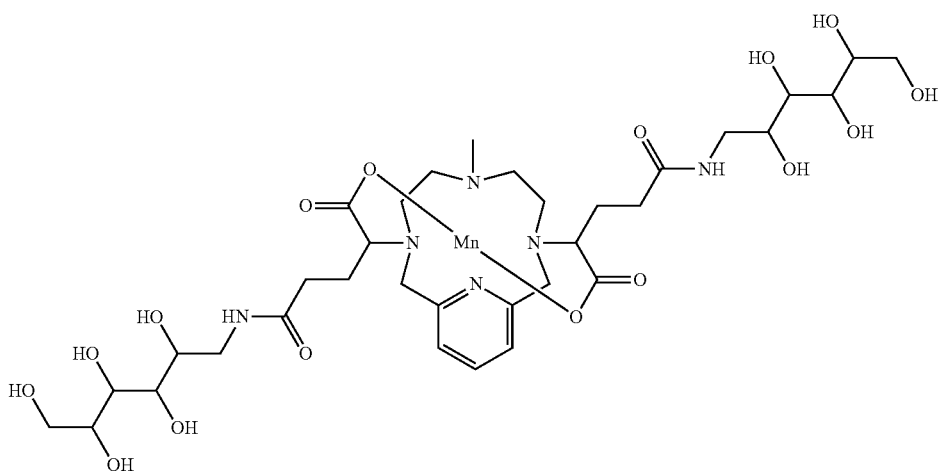
Mn Chelate 5 Racemate

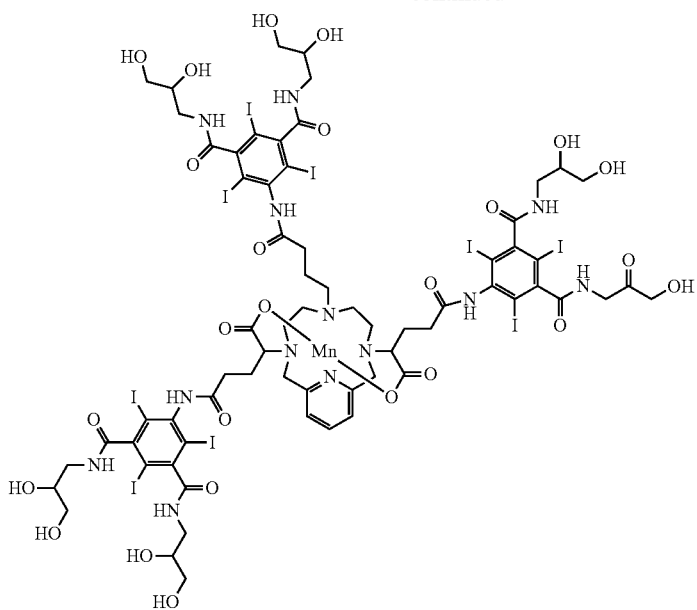
Mn Chelate 6 Racemate
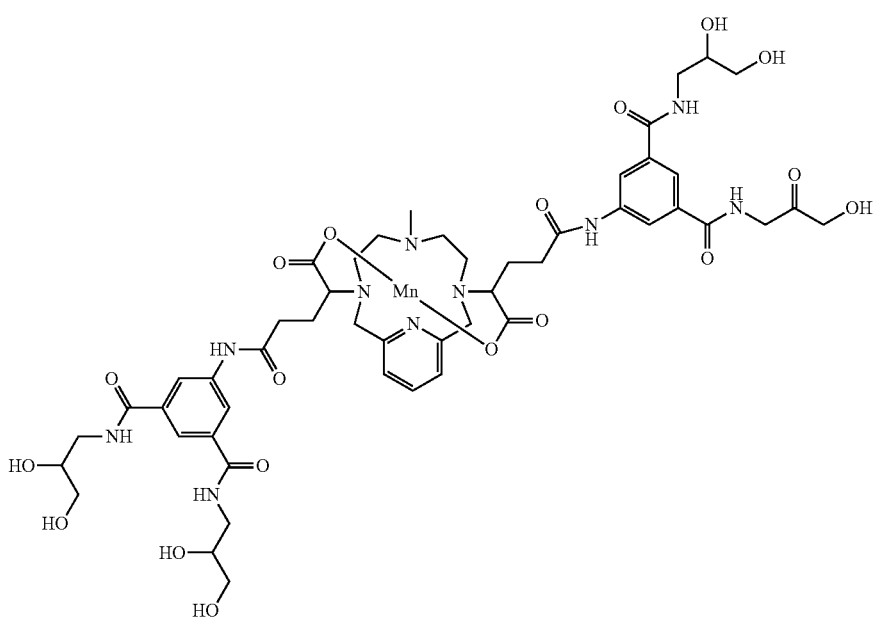
Mn Chelate 7 Racemate

-continued
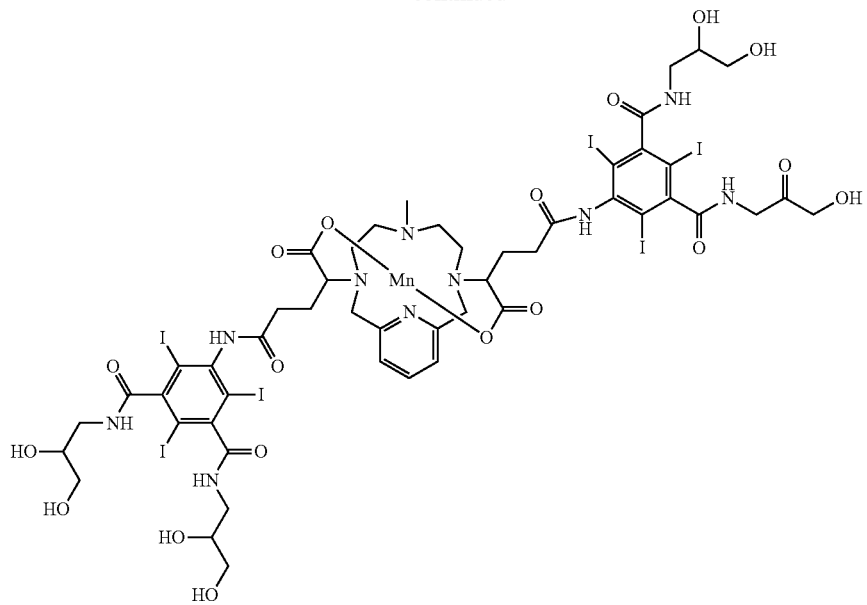
Mn Chelate 8 Racemate
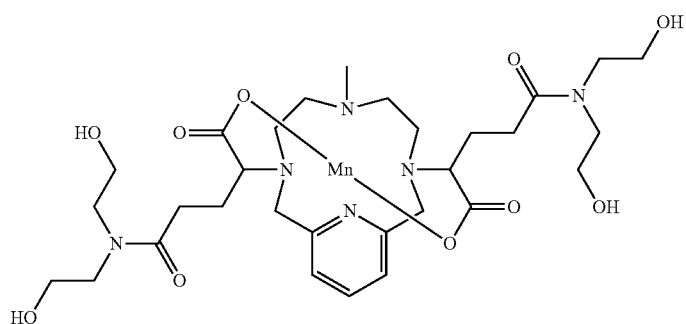
Mn Chelate 9 Racemate
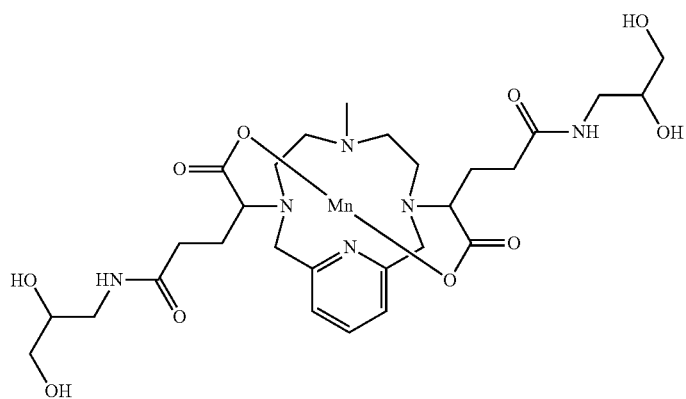
Mn Chelate 10 Racemate -continued
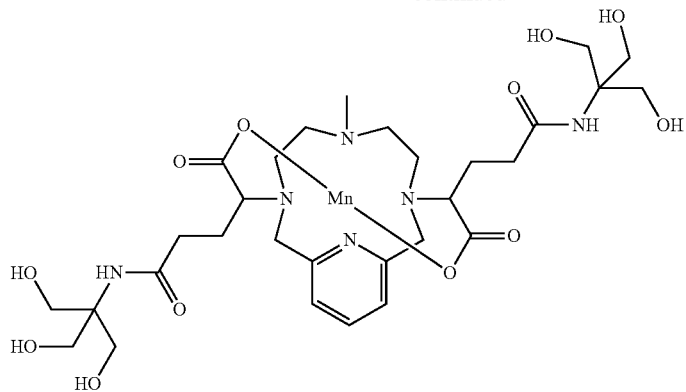
Mn Chelate 11 Racemate
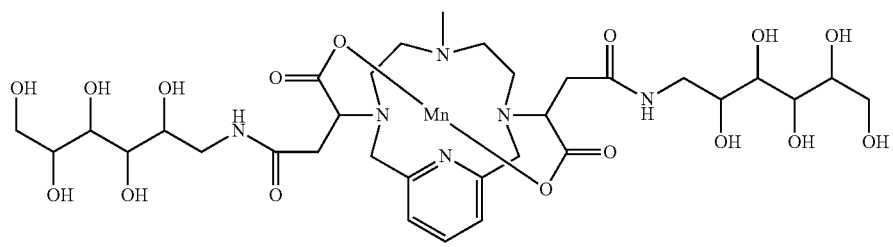
Mn Chelate 5a Racemate
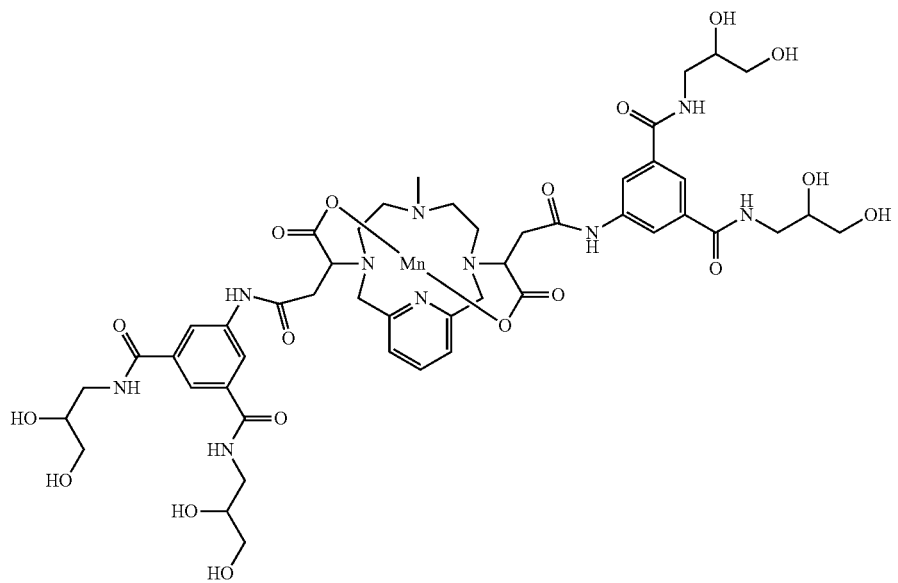
Mn Chelate 7a Racemate -continued

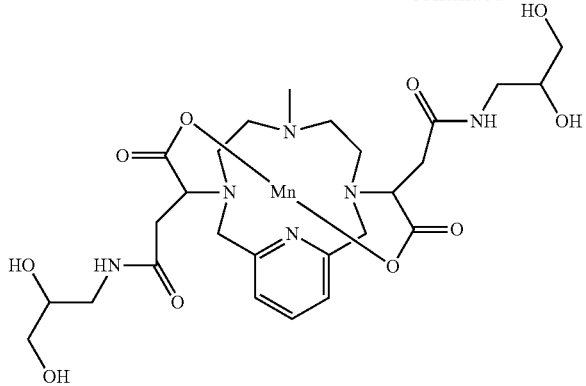

Mn Chelate 10a Racemate

In the compounds of Formula I the carbons attached to the carboxylate arms are stereocentres. The compounds of Formula I of the invention may be provided as racemic mixture or as an enantiomerically-enriched mixture, or the racemic mixture may be separated using well-known techniques and an individual enantiomer may be used alone. In one embodiment, the compound of Formula I is either a racemic mixture or diastereomerically pure. In one embodiment, the compound of Formula I is diastereomerically pure.

Non-limiting examples of diastereomerically pure compounds of Formula I are the following compounds:

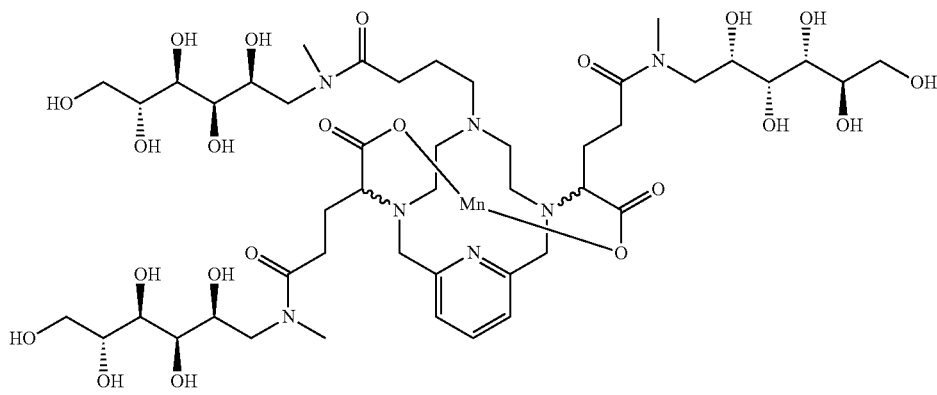

Mn Chelate 3

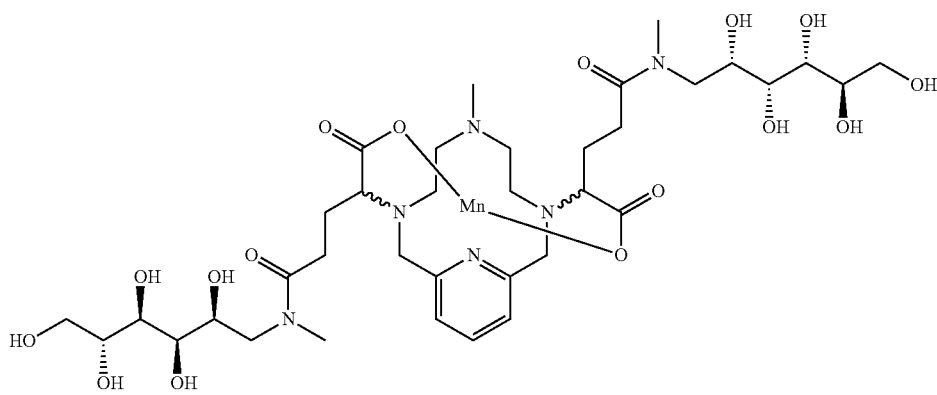

Mn Chelate 4

-continued
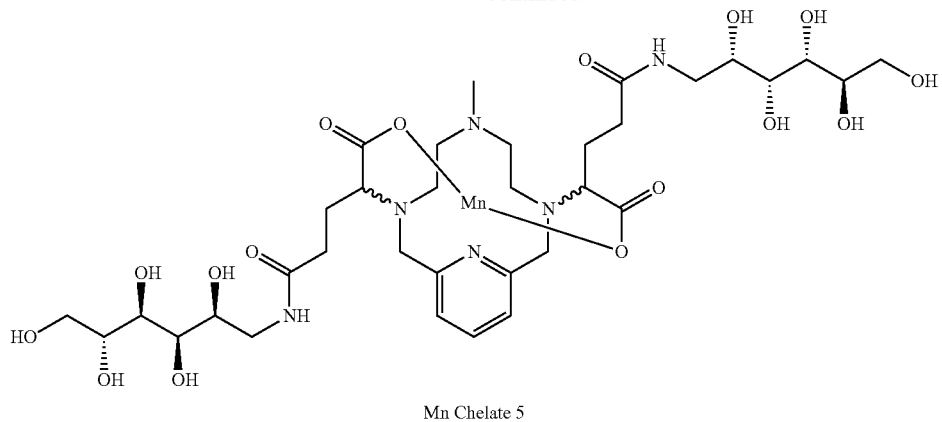
Mn Chelate 5
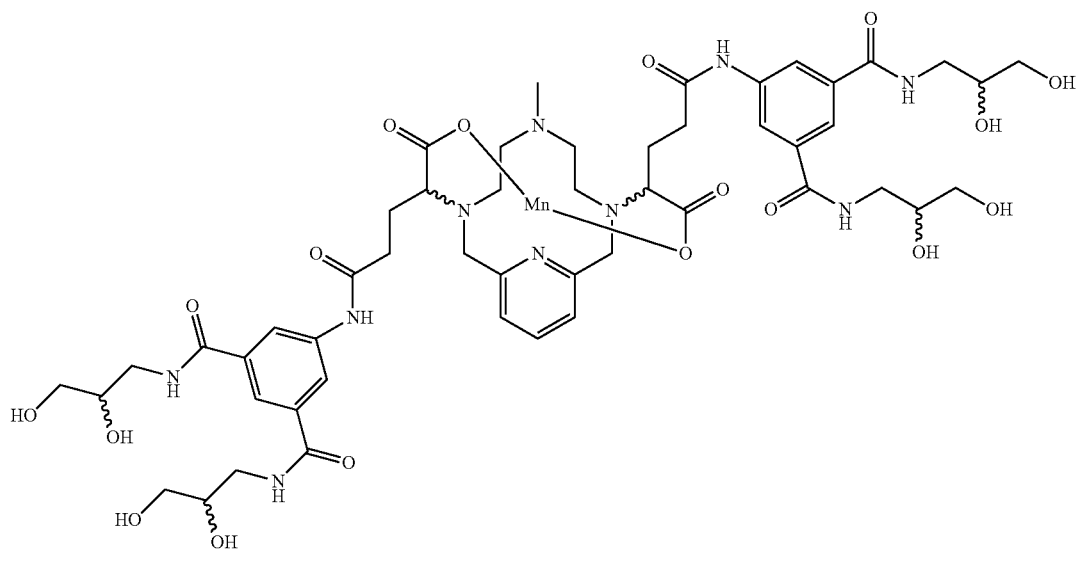
Mn Chelate 7
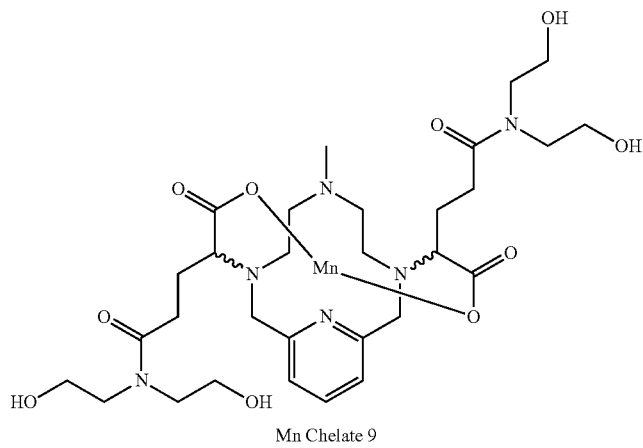
Mn Chelate 9

-continued
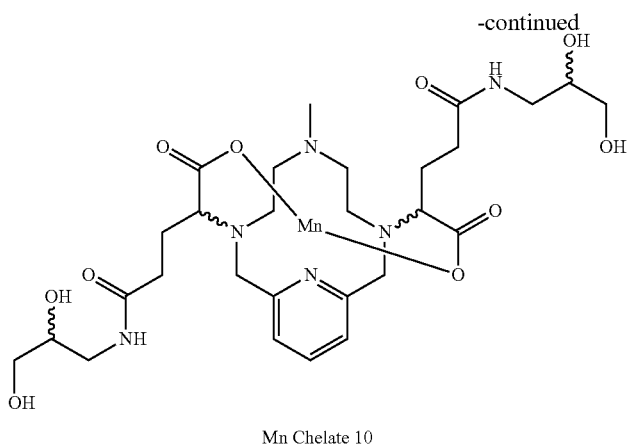
Mn Chelate 10
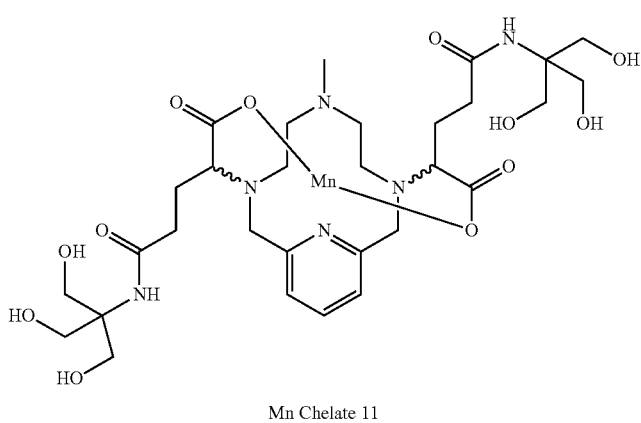
Mn Chelate 11
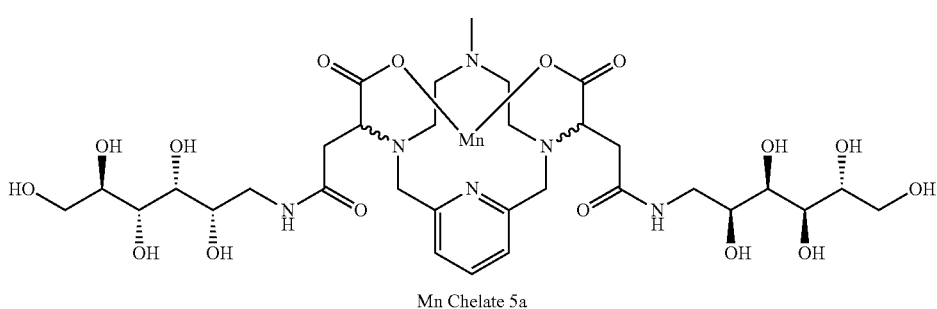
Mn Chelate 5a
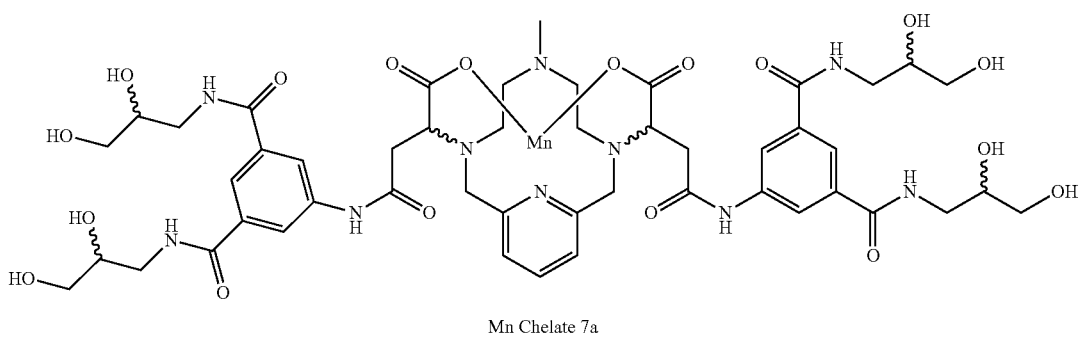
Mn Chelate 7a

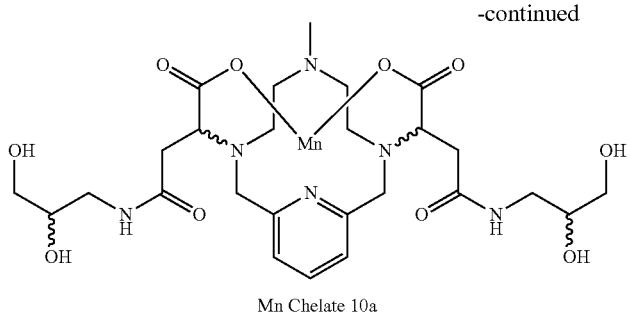

Mn Chelate 10a

Hydrophilic derivatization to obtain the compounds of the invention is achieved via an amide bond to an aliphatic linker. The amide, which is a non-coordinating attachment group, is too distant from the manganese ion and therefore will not coordinate. The exact length of the non-coordinating linker at $R^3$ of Formula I is very important, if too short (i.e. if m=1 in Formula I) there is risk for the amide group coordinating to the manganese ion, thus blocking access of water molecule, dramatically reducing the overall relaxivity of the complex. The length of the non-coordinating linker attached to a carboxymethyl arm (coordinating group) can be short (i.e. where n=0 in Formula I) as the same "arm" is unable to facilitate two coordinating groups (coordination angle will be too strained).

The compounds of Formula I can be synthesized by several synthetic pathways known to the skilled artisan from commercially available starting materials. Suitable sources of manganese for incorporation into a chelate when making compounds of the present invention include salts of carbonate ($MnCO_3$), oxide (MnO), acetate ($Mn(OAc)_2$), chloride ($MnCl_2$), hydroxide ($Mn(OH)_2$), oxalate ($MnC2O_4$), formate ($Mn(HCO_2)_2$) and nitrate ($Mn(NO_3)_2$). The following generalized procedure may be used and/or readily adapted to obtain compounds of Formula I:

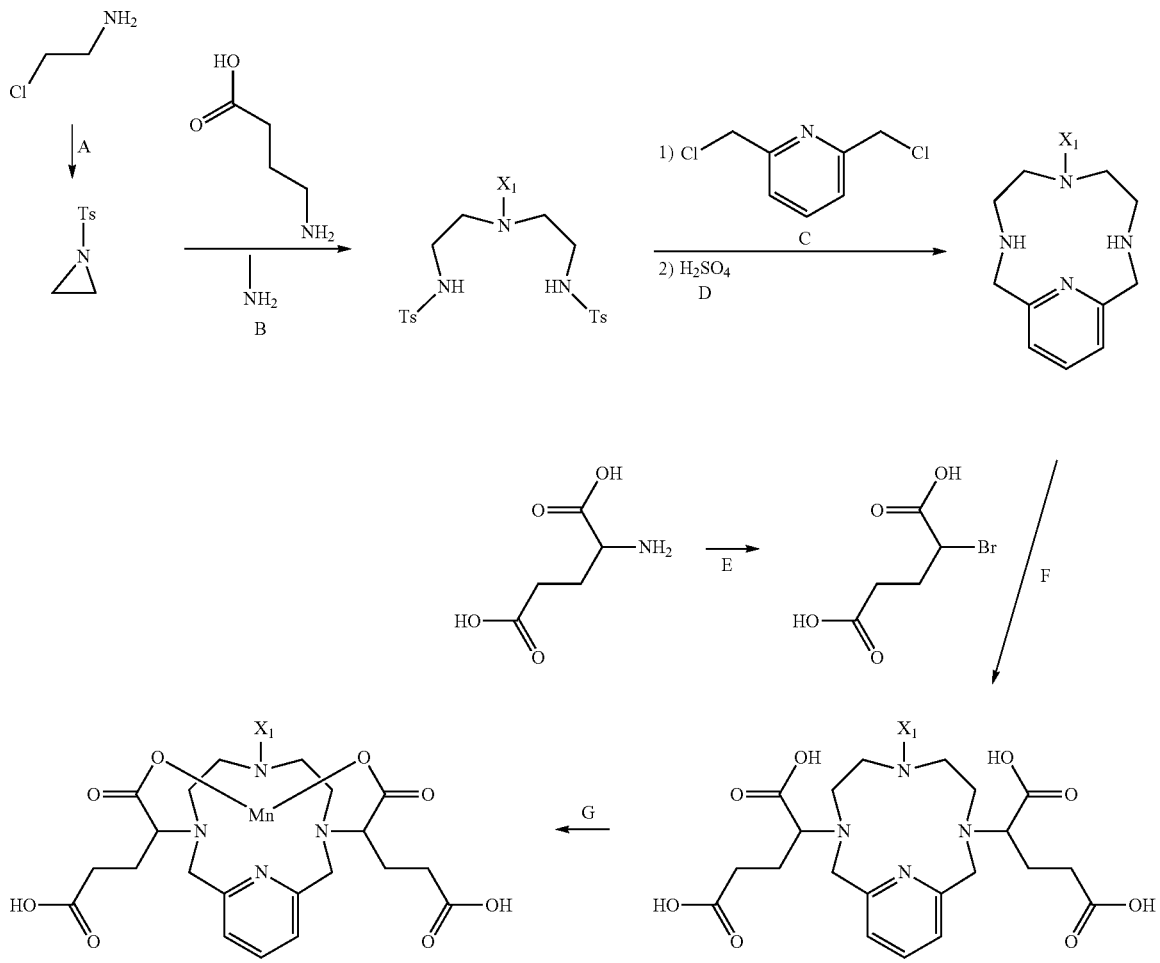

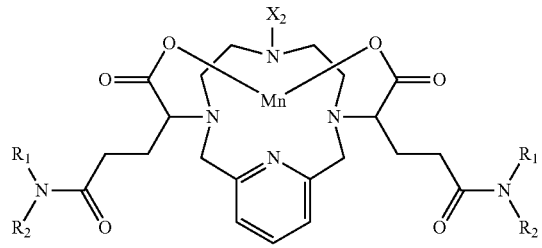

X₁ = CH₃ or CH₂CH₂CH₂COOH
X₂ = CH₃ or CH₂CH₂CH₂CONR₁R₂

In Summary:

A: Tosylation of aminoethanol gives aziridine (Carrillo, Arkivoc, 2007).

B: Aziridation of aminobutanoic acid (Sigma Aldrich catalogue 56-12-2). In one embodiment aziridination of methylamine proceeds in neat acetonitrile). In one embodiment for this amino acid some base is used to activate amine. Optionally the acid functionality could be protected as an ester.

C: Cyclization with 2,6-bis(chloromethyl)-Pyridine (Sigma Aldrich catalogue 3099-28-3). In one embodiment, this step is carried out in acetonitrile with potassium carbonate as the base.

D: De-tosylation using in one embodiment concentrated sulphuric acid. In one embodiment this step proceeds quantitatively.

E: Bromination based on method described in literature (Henig, J., Tóth, É., Engelmann, J., Gottschalk, S., & Mayer, H. a. (2010). Inorganic Chemistry, 49(13), 6124-38).

F: Alkylation of the polyamine. In one embodiment, this step is carried out in aqueous solution. In another embodiment, where secondary halides react sluggishly (primary alkylhalides proceeds well) it is possible to synthesize bis-ester (E) and switch to organic solvent to improve reaction speed.

G: Complexation using MnCl₂. Precipitate excess Mn using base.

H: Activate carboxylates with peptide reagents. In one embodiment, these reagents are EDCl and/or HOBT (as described in EP2457914 B1). Couple with suitable amine (e.g. Meglumine).

Where the compound of Formula I comprises at $R^1$ a substituted aryl such as a triiodated phenyl, the compounds may be obtained using or adapting the following reaction scheme:

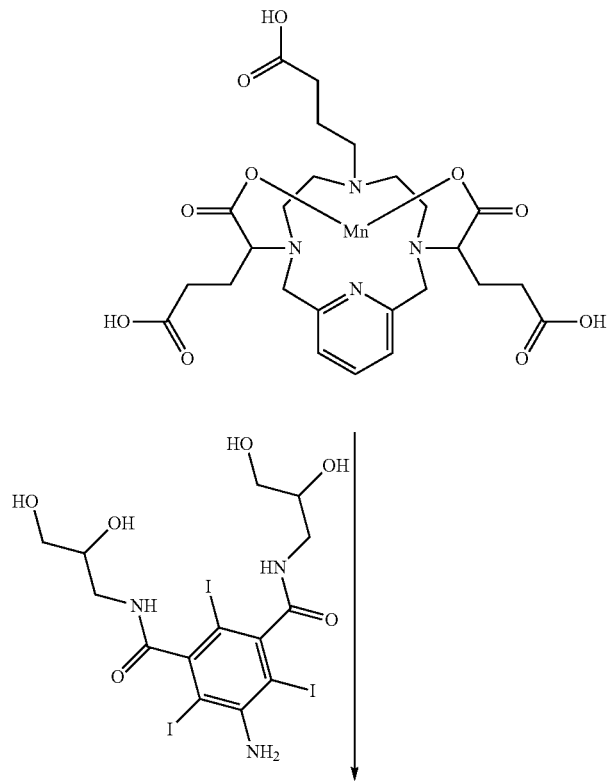

-continued

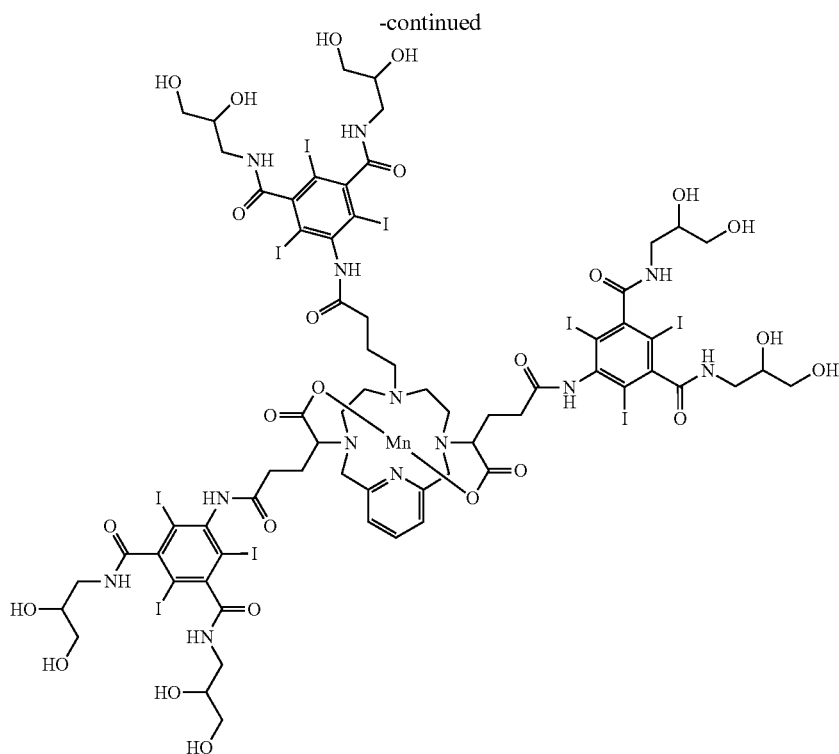

A non-limiting selection of compounds of the invention were synthesised as described below in Examples 1-10 and a compound of the prior art was synthesised as described in Example 11. These compounds were characterised in vitro and/or in vivo as described in Examples 12-15.

Suitable methods for in vitro characterization of chelate stability can be found in the literature (Idée, J. M. Journal of Magnetic Resonance Imaging: JMRI, 2009, 30(6), 1249-58 and Baranyai, Z. Chemistry—A European Journal, 2015, 21(12), 4789-4799). Other suitable methods include in vitro studies of physiological media (i.e. human serum or plasma) to monitor the transmetallation inertness. Another suitable method of assessing transmetallation inertness would be to measure retention of metal ions in vivo, following injection of the chelated metal. It is known that intact chelates normally follows very rapid clearance kinetics.

In one aspect of the invention the compound of Formula I is provided as a pharmaceutical composition.

A "pharmaceutical composition" is a composition comprising the compound of the invention, together with a biocompatible carrier in a form suitable for mammalian administration. The "biocompatible carrier" is a fluid, especially a liquid, in which the compound of Formula I is suspended or dissolved, such that the resulting composition is physiologically tolerable, i.e. can be administered to the mammalian body without toxicity or undue discomfort (which can be understood to be a definition of the term "suitable for mammalian administration").

The pharmaceutical composition of the invention is suitable for use as a magnetic resonance (MR) contrast medium in magnetic resonance imaging (MRI) of the human and non-human animal body.

In one embodiment, the pharmaceutical composition of the invention may comprise one or more pharmaceutically-acceptable excipients. These suitably do not interfere with the manufacture, storage or use of the final composition.

Non-limiting examples of suitable pharmaceutically-acceptable excipients include buffering agents, stabilizers, antioxidants, osmolality adjusting agents, pH adjusting agents, excess cheland and weak complexes of physiologically tolerable ions. These and other suitable excipients will be well known to those of skill in the art and are further described in e.g. WO1990003804, EP0463644-A, EP0258616-A and U.S. Pat. No. 5,876,695 the content of which are incorporated herein by reference. The pharmaceutical composition of the invention in one embodiment is in a form suitable for parenteral administration, for example injection. The pharmaceutical composition according to the invention may therefore be formulated for administration using physiologically acceptable excipients in a manner fully within the skill of the art. For example, the compound of Formula I, optionally with the addition of pharmaceutically acceptable excipients, may be suspended or dissolved in an aqueous medium, with the resulting solution or suspension then being sterilized.

A non-limiting example of a suitable buffering agent is tromethamine hydrochloride.

The term "excess cheland" is defined as any compound capable of scavenging free paramagnetic ion (manganese), but not paramagnetic ion (manganese) retained within the complexes of this invention, as described in EP2988756A1. Although small amounts are essential to human health, overexposure to free manganese ions may result in the neurodegenerative disorder known as "manganism" with symptoms resembling Parkinson's disease. However, the fundamental issue for Mn, as well as other metals, as contrast agents is in their chelation stability. Chelation stability is an important property that reflects the potential release of free metal ions in vivo. It is known that there is a correlation between the amount of excess cheland in a paramagnetic chelate formulation and the amount of paramagnetic metal deposited in animal models (Sieber 2008 J Mag Res Imaging; 27(5): 955-62). Therefore, in another embodiment, an amount of excess cheland is selected that can act as a Mn scavenger to reduce or prevent release of Mn from the formulation post injection. The optimal amount of free cheland will result in a pharmaceutical composition having suitable physicochemical properties (i.e. viscosity, solubility and osmolality) and avoiding toxological effects such as zinc depletion in the case of too much free cheland. U.S. Pat. No. 5,876,695 describes in particular an excess of linear chelate, in particular of free DTPA, and this is a non-limiting example of an excess cheland suitable for use in the pharmaceutical composition of the present invention. This formulation strategy is used for products such as Magnevist™, Vasovist™ or Primovist™. WO2009103744 describes a similar formulation strategy, based on the addition of a precise amount of free chelate, to have a very small excess of said chelate and a zero concentration of free lanthanide.

The physiologically tolerable ion may in one embodiment be selected from physiologically tolerable ions include calcium or sodium salts such as calcium chloride, calcium ascorbate, calcium gluconate or calcium lactate.

Parenterally administrable forms should be sterile and free from physiologically unacceptable agents and should have low osmolality to minimize irritation or other adverse effects upon administration and thus the pharmaceutical composition should be isotonic or slightly hypertonic. Non-limiting examples of suitable vehicles include aqueous vehicles customarily used for administering parenteral solutions such as Sodium Chloride Injection, Ringer's Injection, Dextrose Injection, Dextrose and Sodium Chloride Injection, Lactated Ringer's Injection and other solutions such as are described in Remington's Pharmaceutical Sciences, $22^{nd}$ Edition (2006 Lippincott Williams & Wilkins) and The National Formulary (https://books.google.com/books?id=O3qixPEMwssC&q=THE+NATIONAL+FORMULARY & dq=THE+NATIONAL+FORMULARY & hl=en&sa=X & ved=0CC8Q6A EwAGoVChMlmfPHrdTqyAIVJfNyCh1RJw_E).

For the pharmaceutical composition of the invention to be administered parenterally, i.e. by injection its preparation further comprises steps including removal of organic solvent, addition of a biocompatible buffer and any optional further ingredients such as excipients or buffers. For parenteral administration, steps to ensure that the pharmaceutical composition is sterile and a pyrogenic also need to be taken.

In another embodiment, the present invention provides a method comprising administration of the compound of Formula I as defined herein in the generation of MR images and/or MR spectra.

Methods of administration and subjects envisaged as suitable in the context of the present invention have been described hereinabove in connection with the pharmaceutical composition. Administration of the compound of Formula I is preferably carried out parenterally, and most preferably intravenously. The intravenous route represents the most efficient way to deliver the compound throughout the body of the subject. Furthermore, intravenous administration does not represent a substantial physical intervention or a substantial health risk. The compound of Formula I of the invention is preferably administered as the pharmaceutical composition of the invention, as defined above. The method of the invention can also be understood as comprising steps (ii)-(iii) carried out on a subject to whom the compound of the invention has been pre-administered. In one embodiment, the pharmaceutical composition is administered in an amount suitable to enhance the contrast in a method of MR imaging (MRI). For further detail on MRI methods the reader is referred to the common general knowledge in the art, e.g. as taught in Chapter 27 "Contrast Agents and Magnetic Resonance Imaging" in "Magnetic Resonance Imaging: Physical and Biological Principles" ($4^{th}$ Edition 2015 Elsevier, Stewart Carlyle Bushong & Geoffrey Clarke, Eds.) or in "Contrast Agents I: Magnetic Resonance Imaging" (2002 Springer-Verlang, Werner Krause, Ed.).

The method of the invention may be used to study a biological marker or process in healthy subjects, or alternatively in subjects known or suspected to have a pathological condition associated with abnormal expression of a biological marker. When the method is used to image a subject known or suspected to have a pathological condition it has utility in a method for the diagnosis of said condition.

The "detection" step of the method of the invention involves detection of signals emitted by the compound of Formula I by means of a detector sensitive to said signals. This detection step can also be understood as the acquisition of signal data.

The "generation" step of the method of the invention is carried out by a computer which applies a reconstruction algorithm to the acquired signal data to yield a dataset. This dataset is then manipulated to generate one or more images and/or one or more spectra showing the location and/or amount of signals.

The "subject" of the invention can be any human or animal subject. In one embodiment, the subject of the invention is a mammal. In one embodiment said subject is an intact mammalian body in vivo. In another embodiment, the subject of the invention is a human.

This written description uses examples to disclose the invention, including the best mode, and to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims. All patents and patent applications mentioned in the text are hereby incorporated by reference in their entireties, as if they were individually incorporated.

BRIEF DESCRIPTION OF THE EXAMPLES

Example 1 describes the synthesis of Mn Chelate 3.
Example 2 describes the synthesis of Mn Chelate 4.
Example 3 describes the synthesis of Mn Chelate 5.
Example 4 describes the synthesis of Mn Chelate 7.
Example 5 describes the synthesis of Mn Chelate 9.
Example 6 describes the synthesis of Mn Chelate 10.
Example 7 describes the synthesis of Mn Chelate 11.
Example 8 describes the synthesis of Mn Chelate 5a.
Example 9 describes the synthesis of Mn Chelate 7a.
Example 10 describes the synthesis of Mn Chelate 10a.
Example 11 describes the synthesis of a prior art Mn Chelate.
Example 12 describes in vivo $^{54}$Mn biodistribution studies in rats.
Example 13 describes characterisation of the water solubility of compounds of the invention.

Example 14 describes in vitro proton relaxivity and nuclear magnetic relaxation dispersion (NMRD) profiles of compounds of the invention.

Example 15 describes experiments carried out to determine the dissociation kinetics of compounds of the invention.

LIST OF ABBREVIATIONS USED IN THE EXAMPLES

AcN acetonitrile
DMSO dimethylsulfoxide
EDCl 1-ethyl-3-(3-dimethylaminopropyl)carbodiimide
EtOAc ethyl acetate
EtOH ethanol
h hour(s)
HOBt hydroxybenzotriazole
MeOH methanol
NMR nuclear magnetic resonance
NMRD nuclear magnetic relaxation dispersion

EXAMPLES

Example 1: Synthesis of Mn Chelate 3

Example 1(i): Synthesis of 4-(benzyloxy)-4-oxobutan-1-aminium 4-methylbenzenesulfonate

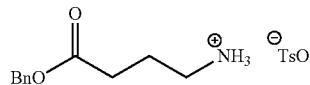

A 2 L 3-necked flask was fitted with a mechanical stirred, a Dean-Stark trap, reflux condenser, and a nitrogen inlet. The flask was charged with 4-aminobutanoic acid (41.522 g, 0.403 mol), p-toluenesulfonic acid (91.912 g, 0.048 mol), and benzyl alcohol (201 mL). The resulting cloudy solution was heated at reflux for 14 h. At the end of the reflux period, n-hepate (175 mL) was added to the hot reaction solution. The reaction was allowed to cool to ambient temperature. The resulting white crystals were isolated via vacuum filtration and recrystallized from 6:1 ethyl acetate/n-hepate to give 124.2 g (84% yield) of the desired product as a white solid. $^1$H NMR (400 MHz, CDCl$_3$, δ) 7.71 (5H, d), 7.31 (5H, m), 7.13 (2H, d), 5.02 (2H, s), 2.87 (2H, m), 2.32 (5H, m), 1.85 (2H, m).

Example 1(ii): Synthesis of benzyl 4-(bis(2-(4-methylphenylsulfonamido)ethyl)amino)butanoate

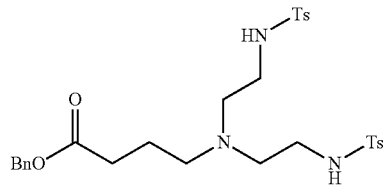 [SMILES: Cc1ccc(S(=O)(=O)NCCN(CCCC(=O)OCc2ccccc2)CCNS(=O)(=O)c2ccc(C)cc2)cc1]

A 2 L jacketed reactor fitted with a 4-blade anchor shaped stir paddle, a reflux condenser, and a nitrogen inlet was charged with N-tosylaziridine (107.7 g, 0.546 mol) and anhydrous acetonitrile (870 mL). 4-(Benzyloxy)-4-oxobutan-1-aminium 4-methylbenzenesulfonate (100 g, 0.274 mol) and anhydrous acetonitrile (500 mL) were then added to give an off white suspension. Diisopropylamine (47.6 mL, 0.274 mol) was added and the reaction was stirred at 40° C. for 16 h. The reaction was then cooled to 22.5° C. and stirred for an additional 49 h. The cloudy white suspension was vacuum filtered and the clear yellow filtrate was evaporated to dryness. The crude material was purified by silica gel chromatography (50% hexanes in EtOAc to 10% hexanes in EtOAc; both eluents contained 1% triethylamine) to give 89.7 g (54%) of the desired product as a colourless oil. $^1$H NMR (400 MHz, CD$_2$Cl$_2$, δ) 7.74 (4H, d), 7.35 (9H, m), 5.13 (2H, m) 5.10 (2H, s), 2.85 (4H, m), 2.41 (10H, m), 2.23 (4H, m), 1.60 (2H, m).

Example 1(iii): Synthesis of Protected Cyclic 3-Arm Chelate

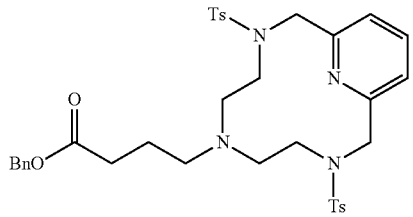 [SMILES: Cc1ccc(S(=O)(=O)N2CCN(CCCC(=O)OCc3ccccc3)CCN(S(=O)(=O)c3ccc(C)cc3)Cc3cccc(n3)C2)cc1]

A 3 L 3-necked round bottomed flask fitted with a mechanical stirrer, a reflux condenser, and a nitrogen inlet was charged with 86 mm diameter glass balls, benzyl 4-(bis(2-(4-methylphenylsulfonamido)ethyl)amino)butanoate (143.9 g, 0.245 mol) and 2,6-Bis(chloromethyl)pyridine (43.1 g, 0.245 mmol). Anhydrous acetonitrile (1.632 L) was added followed by anhydrous potassium carbonate (135.5 g, 0.980 mol) and the resulting solution was heated at 80° C. for 47 h. The resulting suspension was then cooled to ambient temperature and stirred for an additional 65 h. Anhydrous potassium carbonate (67.0 g, 0.485 g) was added and the reaction was stirred at ambient temperature for 27 h. The insoluble potassium carbonate was removed via vacuum filtration and the clear orange filtrate was evaporated to dryness. The crude material was purified by silica gel chromatography (100% CH$_2$Cl$_2$ to 10% MeOH in CH$_2$Cl$_2$; both eluents contained 1% triethylamine) to give 70.9 g (42%) of the desired product as a white foam. $^1$H NMR (400 MHz, CD$_2$Cl$_2$, δ) 7.72 (5H, m), 7.34 (9H, m), 7.26 (2H, d), 5.09 (2H, s), 4.31 (4H, s), 3.07 (4H, m), 2.43 (6H, s), 2.28 (8H, m, 1.61 (2H, m).

Example 1(iv): Synthesis of Deprotected 3-Arm Cyclic Chelate

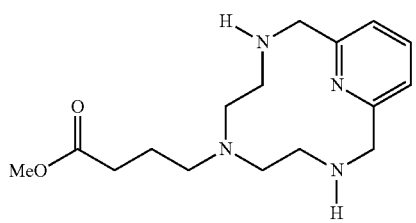

A 3 L 3-necked round-bottomed flask fitted with a mechanical stirrer, a reflux condenser, and a stopper was charged with protected cyclic 3-arm chelate (70.5 g, 92.3 mmol) and concentrated $H_2SO_4$ (282 mL) and heated at 100° for 19 h. The resulting black solution was cooled to ambient temperature and the pH was adjusted to 7 with 50 wt % NaOH in water. MeOH (1 L) was added and the solids were removed via vacuum filtration. The filtrate was concentrated to dryness to leave a black residue which was triturated with MeOH (500 mL) at 60° C. for 1 h. The insoluble material was removed via vacuum filtration and the filtrate was concentrated to dryness. The resulting caramel coloured semisolid was dissolved in MeOH (1 L) and the pH was adjusted to approximately 1 with concentrated $H_2SO_4$ and stirred at ambient temperature for 18 h. The solution was then heated to 60° C. with stirring for 25 h. The insoluble material was removed via vacuum filtration and the pH of the filtrate was adjusted to 7 with potassium carbonate. Undissolved potassium carbonate was removed via vacuum filtration and the filtrate was evaporated to dryness. The resulting off-white solid was triturated with anhydrous acetonitrile (1 L) and the insoluble material was removed via vacuum filtration. The filtrate was evaporated to dryness to give a 25.3 g (89.6%) of the desired product (ESI: m/z=306 (M+H$^+$)) as a white solid.

Example 1(v): Synthesis of Protected Mn 3-Arm C5 Chelate

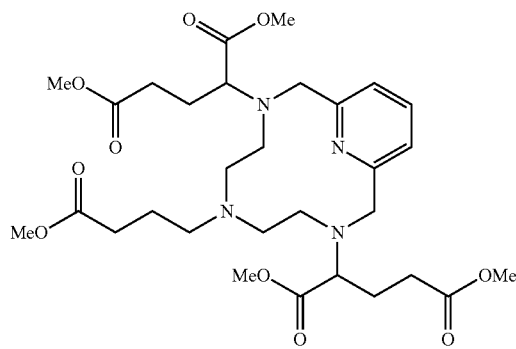 [SMILES: COC(=O)CCCN1CCN(C(CCC(=O)OC)C(=O)OC)Cc2cccc(n2)CN(C(CCC(=O)OC)C(=O)OC)CC1]

A 100 mL round bottomed flask fitted with a magnetic stir bar and a reflux condenser was charged with deprotected 3-arm cyclic chelate (2.776 g, 9.06 mmol) and anhydrous acetonitrile (60.4 mL). Triethylamine (3.16 mL, 22.7 mmol) was then added followed by dimethyl 2-bromopentanedioate (4.982 g, 20.8 mmol) and the resulting solution was heated at 65° C. for 20 h. A second aliquot of dimethyl 2-bromopentanedioate (1.36 g, 5.7 mmol) was added and heating was continued for an additional 23 h. The solvent was removed in vacuo and the crude material was purified on $C_{18}$ silica gel (30% acetonitrile in water) to give 2.883 g (51%) of the desired product (ESI: m/z=623 (M+H$^+$)) as a yellow oil.

Example 1(vi): Synthesis of Deprotected Mn 3-Arm C5 Chelate

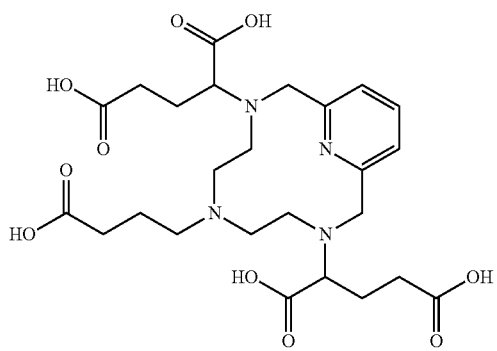 [SMILES: O=C(O)CCCN1CCN(C(CCC(=O)O)C(=O)O)Cc2cccc(n2)CN(C(CCC(=O)O)C(=O)O)CC1]

A 500 mL round bottomed flask fitted with a magnetic stir bar was charged with protected Mn 3-arm C5 chelate (14.010 g, 22.5 mmol) dissolved in water (225 mL) and 12.5 M NaOH (18.0 mL) was added. The resulting solution was stirred at ambient temperature for 18 h. The pH was then adjusted to 6 with conc. HCl and the solvent was removed in vacuo. The crude residue was purified on C18 silica gel (100% water to 15% AcN in water) to give 12.43 g (100%) of the desired product (ESI: m/z=553 (M+H$^+$)) as a yellow oil.

Example 1(vii): Synthesis of Mn 3-Arm C5 Chelate

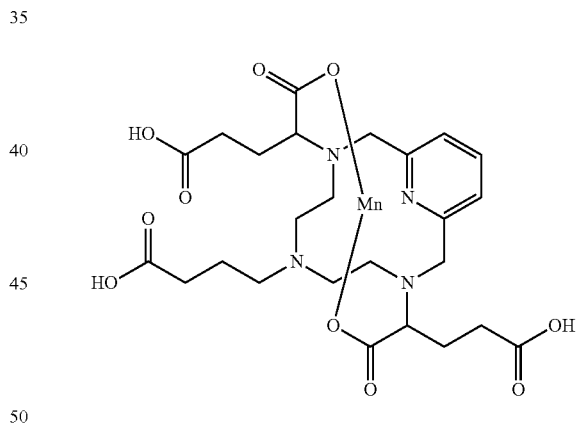

A 1 L 3-necked round bottomed flask fitted with a magnetic stir bar was charged with deprotected Mn 3-arm C5 chelate (12.43 g, 22.5 mmol), manganese chloride tetrahydrate (8.90 g, 45.1 mmol) and water (405 mL). The resulting solution was stirred at ambient temperature for 12.5 h. The pH was then adjusted to 6 and the reaction was heated at 75° C. for 7 h. The solution was cooled to ambient temperature and the pH was adjusted to 8 with saturated aqueous sodium carbonate. The resulting white precipitate was removed via vacuum filtration and the filtrate was evaporated to dryness in vacuo. The crude residue was purified on $C_{18}$ silica gel (100% water) to give 13.33 g (98%) of the desired product (ESI: m/z=606 (M+H$^+$)) as a yellow solid.

Example 1(viii): Synthesis of Mn Chelate 3

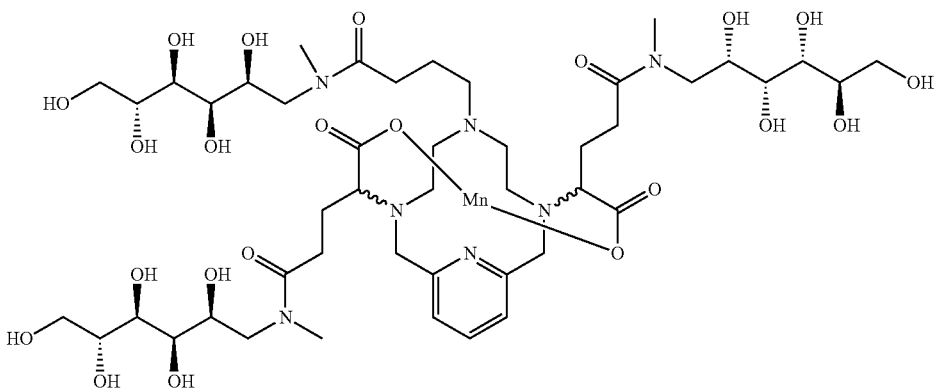

A 100 mL 3-necked flask fitted with a mag stir bar was charged with Mn 3-arm C5 chelate (1.54 g, 2.5 mmol) and dissolved water (26.8 mL). N-methyl-D-glucamine (1.54 g, 7.9 mmol) was added followed by EDCl-HCl (1.64 g, 8.6 mmol) and the pH was adjusted to 6.4 with 1.0 M HCl. HOBt hydrate (0.140 g, 1.0 mmol) was added and the pH was maintained at 6 while stirring at ambient temperature for 18 h. N-methyl-D-glucamine (0.77 g, 3.9 mmol) and EDCl-HCl (0.82 g, 4.3 mmol) were and the pH was maintained at 6 while stirring at ambient temperature for 8 h. EDCl-HCl (0.42 g, 2.2 mmol) was added and stirred at ambient temperature for 17 h. All solvent was then removed in vacuo to leave a brown oil that was purified on $C_{18}$ silica gel (100% water to 30% AcN in water) to give 1.6 g (56%) of the desired product (ESI: m/z=1138 (M+H$^+$)).

Example 2: Synthesis of Mn Chelate 4

Example 2(i): Synthesis of N,N'-((methylazanediyl)bis(ethane-2,1-diyl))bis(4-methylbenzenesulfonamide)

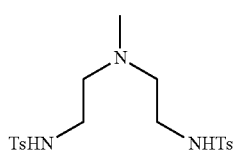

A 1 L round bottomed flask fitted with a magnetic stir bar was charged with N-tosylaziridine (49 g, 248 mmol) and AcN (450 mL). 41% aqueous methylamine (12 mL, 121 mmol) was added and stirred at ambient temperature for 36 h. A second aliquot of N-tosylaziridine (1.7 g, 8.62 mmol) was added and stirred at ambient temperature for an additional 48 h. The solvent was removed in vacuo and the crude residue was recrystallized from EtOH to give 45 g (87%) of the desired product as a white solid. $^1$H NMR (400 MHz, DMSO-D$_6$, δ) 7.68 (4H, m), 7.36 (6H, m), 2.75 (4H, t), 2.38 (6H, s), 2.22 (4H, t), 1.93 (3H, s).

Example 2(ii): Synthesis of Protected Cyclic 2-Arm Chelate

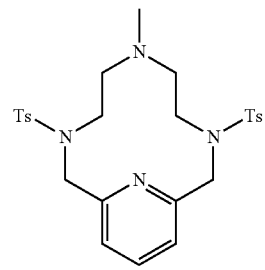 [SMILES: Cc1ccc(S(=O)(=O)N2CCN(C)CCN(S(=O)(=O)c3ccc(C)cc3)Cc3cccc(n3)C2)cc1]

A 12 L 3-necked round bottomed flask fitted with a reflux condenser and a mechanical stirrer was charged with N,N'-((methylazanediyl)bis(ethane-2,1-diyl))bis(4-methylbenzenesulfonamide (93 g, 218.5 mmol) and AcN (8.3 L). 2,6-bis(chloromethyl)pyridine (38.5 g, 218.5 mmol) was added and the resulting solution was heated at 80° for 16 h. The reaction mixture was cooled to ambient temperature and solvent was removed in vacuo until crystallization began. The resulting crystals were collected via vacuum filtration to afford 86.9 g (75%) of the desired product as a white solid (ESI: m/z=530 (M+H$^+$)).

Example 2(iii): Synthesis of Deprotected 2-Arm Cyclic Chelate

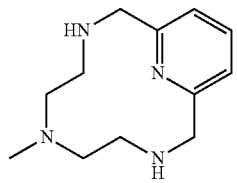 [SMILES: CN1CCNCc2cccc(n2)CNCC1]

A 1 L 3-necked round bottomed flask fitted with a mechanical stirrer was charged with protected cyclic 2-arm chelate (150 g, 284 mmol) and concentrated sulfuric acid (250 mL, 4.69 mol) and heated at 100° C. for 15 h. The solution was poured onto ice and the pH was adjusted to 7.4 with the addition of 50 wt % NaOH in water resulting in the formation of a white solid. AcN (200 mL) was added and the white solid was removed via vacuum filtration. The filtrate was evaporated to dryness to give a brown foam. The foam was dissolved in water (200 mL) and purified with Amberlite A26 resin in its hydroxide form to give 61 g (98%) of the desired product as a tan solid. $^1$H NMR (400 MHz, CD$_3$CN, δ) 7.56 (1H, m), 7.03 (2H, m), 3.76 (4H, s), 2.47 (4H, m), 2.19 (3H, s), 1.95 (4H, s).

Example 2(iv): Synthesis of Protected Mn 2-Arm C5 Chelate

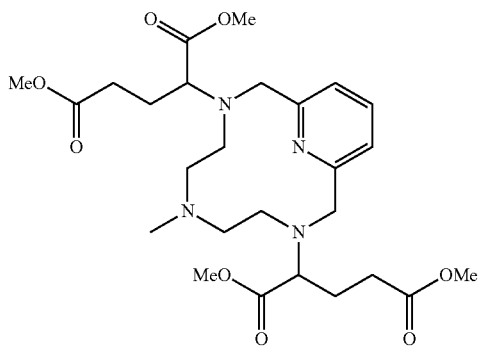 [SMILES: COC(=O)CCC(C(=O)OC)N1CCN(C)CCN(C(CCC(=O)OC)C(=O)OC)Cc2cccc(n2)C1]

A 500 mL round bottomed flask fitted with a magnetic stir bar was charged with deprotected 2-arm cyclic chelate (20.0 g, 90.8 mmol; obtained according to Example 2(iii)) and AcN (160 mL). Diisopropylethylamine (38.7 mL, 217 mmol) and dimethyl 2-bromopentanedioate (47.7 g, 199.7 mmol) were added and the resulting solution was stirred at 65° C. for 20 h. Diisopropylethylamine (9.75 mL, 54.6 mmol) and dimethyl 2-bromopentanedioate (11.8 g, 49.4 mmol) were added and the resulting solution was stirred at 65° C. for an additional 19 h. The solvent was removed in vacuo to leave a red oil. The oil was then dissolved in water (300 mL) and washed with EtOAc (300 mL). The EtOAc layer was then extracted with water (2×50 mL) and combined with the initial aqueous layer and the water was removed in vacuo to leave a red oil was used without further purification.

Example 2(v): Synthesis of Mn 2-Arm C5 Chelate

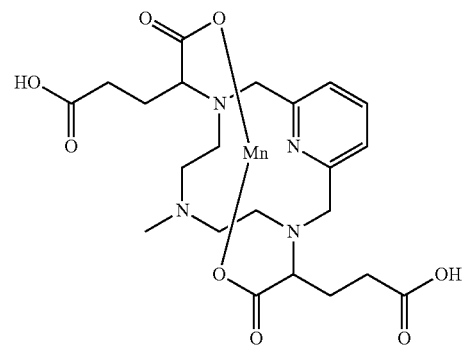

A 1 L round bottomed flask fitted with a magnetic stir bar was charged with protected Mn 2-arm C5 chelate (48.7 g, 90.8 mmol) and water (450 mL). Sodium hydroxide (29.1 g, 726 mmol) was added and stirred at ambient temperature for 2 h. The reaction mixture was washed with EtOAc (250 mL) and the layers were separated. The aqueous layer was washed again with EtOAc (2×100 mL) and the aqueous layer was collected. Manganese chloride tetrahydrate (19.6 g, 99 mmol) was added to the aqueous solution. The pH was adjusted to 7.1 with 6 M NaOH and stirred at ambient temperature for 17 h and then at 90° C. for 2.5 h. After cooling to ambient temperature, the pH was adjusted to 10.1 with 50 wt % aqueous NaOH and a fine brown precipitate formed. The precipitate was removed via centrifugation at 3000 rcf for 20 min and the supernatant was collected and evaporated to dryness in vacuo. The residue was triturated with MeOH (127 mL) at 40° C. for 1.5 h. The insoluble white solid was removed via centrifugation at 3000 rcf for 30 min. The supernatant was evaporated to dryness in vacuo to give an off-white solid which was purified on C$_{18}$ silica gel (3% AcN in water) to give 36.8 g (75%) of the desired product as an off white solid (ESI: m/z=534 (M+H$^+$)).

Example 2(vi): Synthesis of Mn Chelate 4

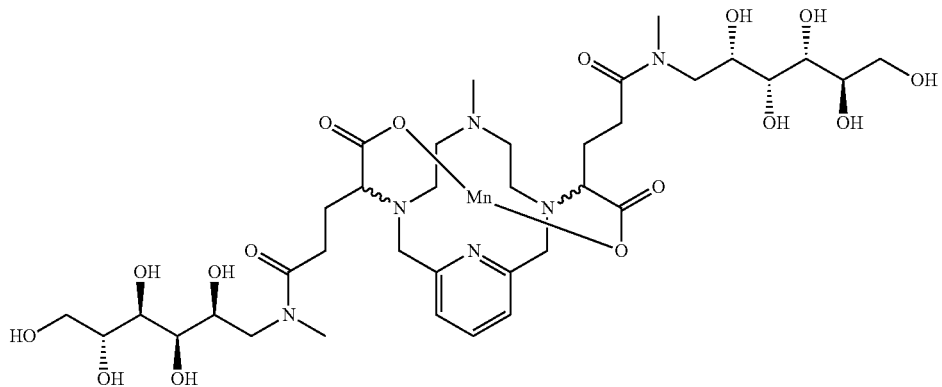

A 250 mL 3-necked round bottomed flask fitted with a magnetic stir bar was charged with Mn 2-arm C5 chelate (4.40 g, 7.27 mmol) and water (76.5 mL). N-methyl-D-glucamine (2.98 g, 15.3 mmol) was added followed by EDCl-HCl (3.30 g, 17.2 mmol) and HOBt hydrate (0.20 g, 1.47 mmol). The pH was maintained at 6 with addition of 1.0 M HCl or 1.0 M NaOH as needed while stirring at ambient temperature for 7 h. EDCl-HCl (1.62 g, 8.45 mmol) was added and the pH was maintained at 6 while stirring for 20 h at ambient temperature. N-methyl-D-glucamine (0.75 g, 3.84 mmol) and EDCl-HCl (0.83 g, 4.32 mmol) were added and the pH was maintained at 6 while stirring at ambient temperature for 3 d. The reaction solution was evaporated to dryness in vacuo and the crude product was purified on $C_{18}$ silica gel (100% water to 20% AcN in water) to give 3.66 g (57%) of the desired product as a pale yellow solid (ESI: m/z=888 (M+H$^+$)).

Example 3: Synthesis of Mn Chelate 5

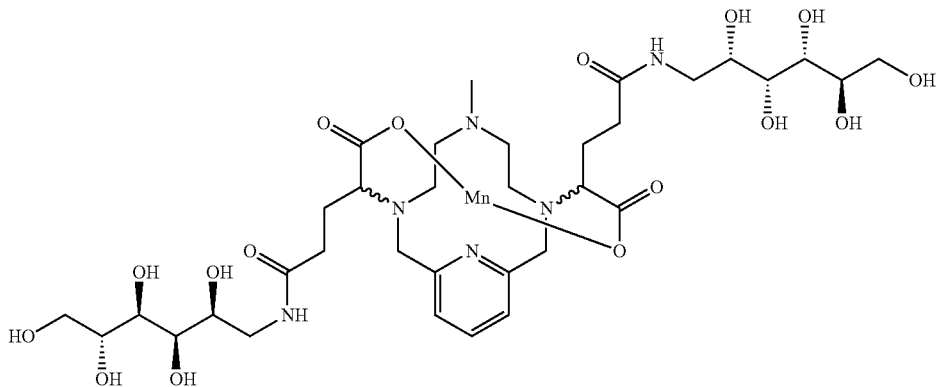

A 50 mL 2-necked flask fitted with a magnetic stir bar was charged with D-glucamine (0.713 g, 3.94 mmol) and water (19.7 mL). The pH of the resulting solution was adjusted to 7.4 with 1.0 M HCl and Mn 2-arm C5 chelate (1.00 g, 1.87 mmol; obtained according to Example 2(v)) was added followed by EDCl-HCl (0.848 g, 4.42 mmol) and HOBt hydrate (0.121 g, 0.787 mmol). The pH was maintained at 6 with addition of 1.0 M HCl or 1.0 M NaOH as needed while stirring at ambient temperature for 8 h. D-Glucamine (0.359 g, 1.98 mmol) and EDCl-HCl (0.433 g, 2.26 mmol)) were added and the pH was maintained at 6 while stirring at ambient temperature for 16 h. The reaction solution was evaporated to dryness in vacuo and the crude product was purified on $C_{18}$ silica gel (100% water to 20% AcN in water) to give 0.782 g (48%) of the desired product as a pale yellow solid (ESI: m/z=860 (M+H$^+$)).

Example 4: Synthesis of Mn Chelate 7

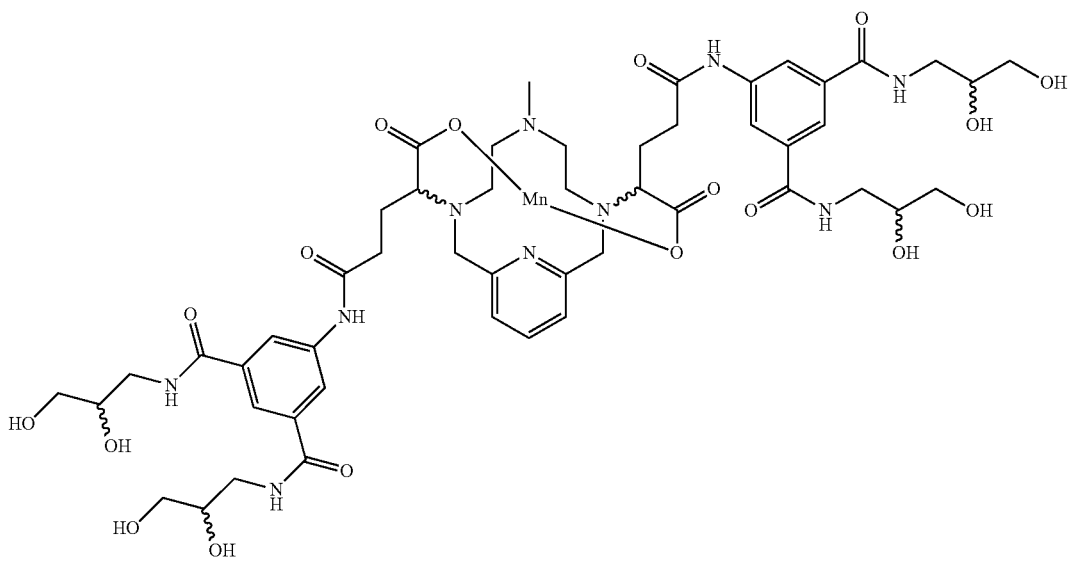

A 2-necked 50 mL flask fitted with a magnetic stir bar was charged with 5-amino-N,N'-bis(2,3-dihydroxypropyl)isophthalamide hydrochloride (1.432 g, 3.94 mmol) and water (19.7 mL). The pH of the resulting solution was adjusted to 6 and Mn 2-arm C5 chelate (1.005 g, 1.88 mmol; obtained according to Example 2(v)) was added followed by EDCl-HCl (0.858 g, 4.48 mmol) and HOBt hydrate (0.108 g, 0.799 mmol). The pH was maintained at 6 with addition of 1.0 M HCl or 1.0 M NaOH as needed while stirring at ambient temperature for 4.5 h. EDCl-HCl (0.868 g, 4.53 mmol) was added and the pH was maintained at 6 while stirring at ambient temperature for 16 h. EDCl-HCl (0.853 g, 4.44 mmol) and the pH was maintained at 6 while stirring at ambient temperature for 7 h. The reaction solution was evaporated to dryness in vacuo and the crude product was purified on $C_{18}$ silica gel (100% water to 25% AcN in water) to give 0.600 g (28%) of the desired product as a pale yellow solid (ESI: m/z=1152 ($M^+$)).

Example 5: Synthesis of Mn Chelate 9

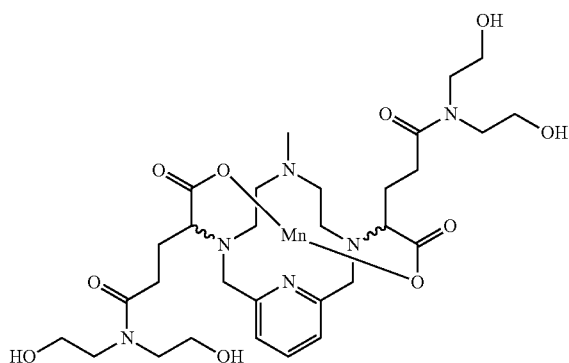

A 2-necked 25 mL flask fitted with a magnetic stir bar was charged with diethanolamine (0.207 g, 1.97 mmol) and water (9.86 mL). The pH of the resulting solution was adjusted to 7 with 1.0 M HCl and Mn 2-arm C5 chelate (0.500 g, 0.956 mmol; obtained according to Example 2(v)) was added followed by EDCl-HCl (0.445 g, 2.32 mmol) and HOBt hydrate (0.045 g, 0.333 mmol). The pH was maintained at 6 with addition of 1.0 M HCl or 1.0 M NaOH as needed while stirring at ambient temperature for 20 h. Diethanolamine (0.207 g, 1.97 mmol) and EDCl-HCl (0.432 g, 2.25 mmol) were added and the pH was maintained at 6 while stirring at ambient temperature for 8 h. Diethanolamine (0.207 g, 1.97 mmol) and EDCl-HCl (0.448 g, 2.34 mmol) were added and the pH was maintained at 6 while stirring at ambient temperature for 15.5 h. The reaction solution was evaporated to dryness in vacuo and the crude product was purified on $C_{18}$ silica gel (100% water to 30% AcN in water) to give 0.110 g (16%) of the desired product as a pale yellow solid (ESI: m/z=708 ($M+H^+$)).

Example 6: Synthesis of Mn Chelate 10

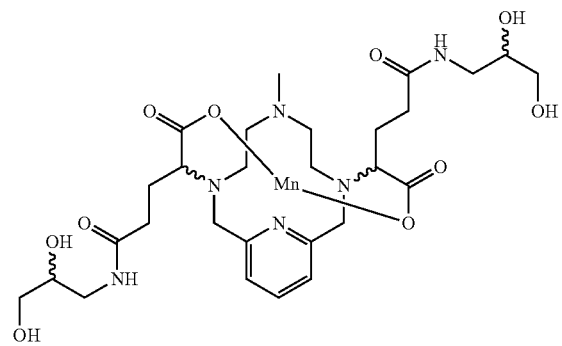

A 25 mL 2-necked flask fitted with a magnetic stir bar was charged with 3-aminopropane-1,2-diol (0.190 g, 2.03 mmol) and water (10.4 mL). The pH of the resulting solution was adjusted to 7 with 1.0 M HCl and Mn 2-arm C5 chelate (0.603 g, 0.996 mmol; obtained according to Example 2(v)) was added followed by EDCl-HCl (0.473 g, 2.47 mmol) and HOBt hydrate (0.063 g, 0.466 mmol). The pH was maintained at 6 with addition of 1.0 M HCl or 1.0 M NaOH as needed while stirring at ambient temperature for 7.5 h. 3-Aminopropane-1,2-diol (0.095 g, 1.04 mmol) and EDCl-HCl (0.453 g, 2.36 mmol) were added and the pH was maintained at 6 while stirring at ambient temperature for 15.5 h. The reaction solution was evaporated to dryness in vacuo and the crude product was purified on $C_{18}$ silica gel (100% water to 20% AcN in water) to give 0.280 g (41%) of the desired product as a pale yellow solid (ESI: m/z=680 ($M+H^+$)).

Example 7: Synthesis of Mn Chelate 11

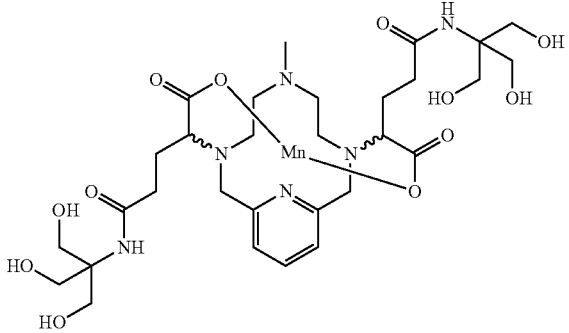

A 100 mL 3-necked round bottomed flask fitted with a magnetic stir bar was charged with Tris base (0.632 g, 5.22 mmol) and water (26.0 mL). The pH of the resulting solution was adjusted to 7 with 1.0 M HCl and Mn 2-arm C5 chelate (1.500 g, 2.49 mmol; obtained according to Example 2(v)) was added followed by EDCl-HCl (1.141 g, 5.95 mmol) and HOBt hydrate (0.160 g, 1.04 mmol). The pH was maintained at 6 with addition of 1.0 M HCl or 1.0 M NaOH as needed while stirring at ambient temperature for 7.5 h. Tris (0.636 g, 5.25 mmol) and EDCl-HCl (1.177 g, 6.14 mmol) were added and the pH was maintained at 6 while stirring at ambient temperature for 17 h. Tris (0.624 g, 5.15 mmol) and EDCl-HCl (1.133 g, 5.91 mmol) were added and the pH was maintained at 6 while stirring at ambient temperature for 23 h. The reaction solution was evaporated to dryness in vacuo and the crude product was purified on $C_{18}$ silica gel (100% water to 20% AcN in water) to give 0.247 g (13%) of the desired product as a pale yellow solid (ESI: m/z=740 ($M+H^+$)).

Example 8: Synthesis of Mn Chelate 5a

Example 8(i): Synthesis of Protected Mn 2-Arm C4 Chelate

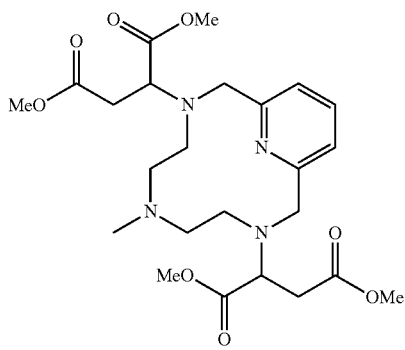 [SMILES: COC(=O)CC(C(=O)OC)N1CCN(C)CCN(C(CC(=O)OC)C(=O)OC)Cc2cccc(n2)C1]

A 250 mL round bottomed flask fitted with a mechanical stirrer was charged with 2-arm cyclic chelate (19.85 g, 90.1 mmol; obtained according to Example 2(iii)), dimethyl maleate (51.94 g, 360.4 mmol), Montmorillonite K10 (36.0 g), and MeOH (36 mL). The resulting suspension was stirred at ambient temperature for 26 h. The insoluble material was removed via filtration and the clear orange filtrate was evaporated to dryness. The residue was dissolve in EtOAc (200 mL) and extracted with water (200 mL). The layers were separated and the aqueous layer was evaporated to dryness to give 39.35 g (86%) as an orange solid (ESI: m/z=509 (M+H$^+$)) which was used without further purification.

Example 8(ii): Synthesis of Mn 2-Arm C4 Chelate

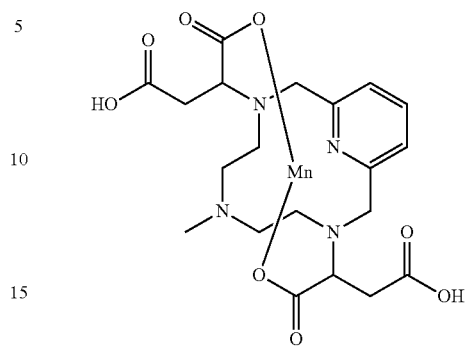

A 1 L round bottomed flask fitted with a magnetic stir bar was charged with protected Mn 2-arm C4 chelate (39.35 g, 77.2 mmol), sodium hydroxide (24.71 g, 617 mmol) and water (500 mL). The resulting solution was stirred at 45° C. for 4 h. The pH was adjusted to 7 with concentrated HCl and MnCl$_4$-4H$_2$O (16.8 g, 84.9 mmol) was added. The pH was maintained at 7 while stirring at 90° C. for 2.5 h before cooling to ambient temperature. The pH was adjusted to 10.1 with 6.0 M NaOH and the resulting precipitate removed via centrifugation at 3000 rcf for 20 min. The supernatant was collected and evaporated to dryness in vacuo. The residue was triturated with MeOH (72 mL) at 40° C. for 1.5 h. The insoluble white solid was removed via centrifugation at 3000 rcf for 30 min. The supernatant was evaporated to dryness in vacuo to give an off-white solid which was purified on C$_{18}$ silica gel (3% AcN in water) to give 25.8 g (66%) of the desired product as an off white solid (ESI: m/z=506 (M+H$^+$)).

Example 8(iii): Synthesis of Mn Chelate 5a

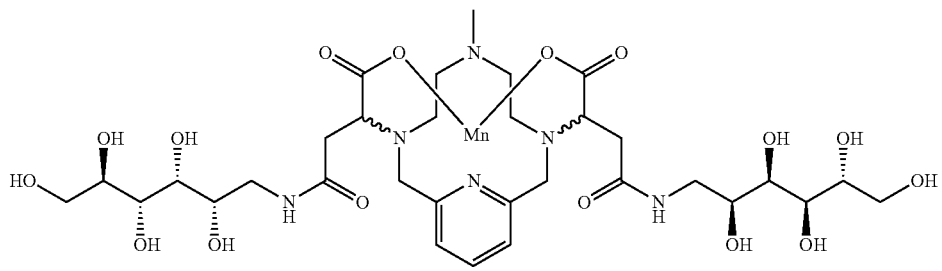

A 2-necked 50 round bottomed flask fitted with a magnetic stir bar was charged with Mn 2-arm C4 chelate (0.667 g, 1.32 mmol) and water (13.0 mL). Glucamine (0.505 g, 2.79 mmol) was added and the pH was adjusted to 7 with 1.0 M HCl. EDCl-HCl (0.599 g, 3.12 mmol) and HOBt hydrate (0.036 g, 0.266 mmol) were added and the pH was maintained at 6 with addition of 1.0 M HCl or 1.0 M NaOH as needed while stirring at ambient temperature for 7.5 h. A second aliquot of EDCl-HCl (0.610 g, 3.18 mmol) was added and the pH was maintained at 6 while stirring at ambient temperature for 16.5 h. A third aliquot of EDCl-HCl (0.610 g, 3.18 mmol) was added and the pH was maintained at 6 while stirring at ambient temperature for 72 h. The reaction solution was evaporated to dryness in vacuo and the crude product was purified on C$_{18}$ silica gel (100% water to 30% AcN in water) to give 0.350 g (31%) of the desired product as a pale yellow solid (ESI: m/z=832 (M+H$^+$)).

Example 9: Synthesis of Mn Chelate 7a

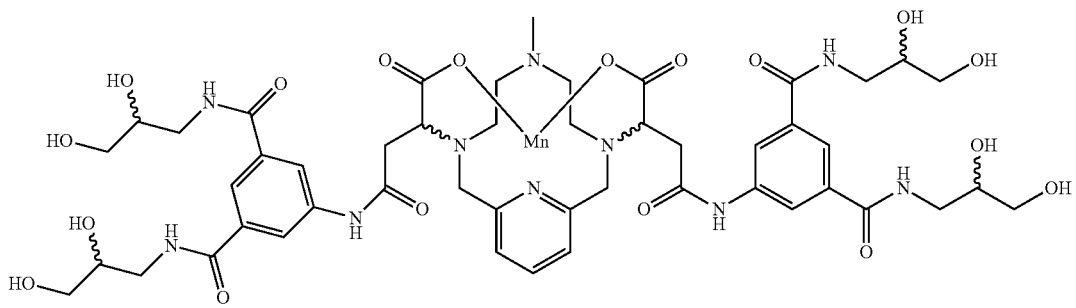

A 3-necked 100 mL round bottomed flask fitted with a magnetic stir bar was charged with 5-Amino-N,N'-bis(2,3-dihydroxypropyl).

isophthalamide hydrochloride (1.516 g, 4.17 mmol) and water (20 mL). The pH of the resulting solution was adjusted to 8 with 1.0 M NaOH and Mn 2-arm C4 chelate (1.000 g, 1.98 mmol; obtained according to Example 8(ii)) was added followed by EDCl-HCl (0.901 g, 4.70 mmol). The pH was maintained at 6 with addition of 1.0 M HCl or 1.0 M NaOH as needed while stirring at ambient temperature for 6.5 h. A second aliquot of EDCl-HCl (0.895 g, 4.67 mmol) was added and the pH was maintained at 6 while stirring at ambient temperature for 16.5 h. A third aliquot of EDCl-HCl (0.417 g, 2.18 mmol) was added and the pH was maintained at 6 while stirring at ambient temperature for 8 h. A fourth aliquot of EDCl-HCl (0.536 g, 2.80 mmol) was added and the pH was maintained at 6 while stirring at ambient temperature for 17 h. The cloudy reaction mixture was vacuum filtered to remove the solids. The clear, yellow filtrate was evaporated to dryness and the crude product was purified on $C_{18}$ silica gel (100% water to 20% AcN in water) to give 0.494 g (22%) of the desired product as a pale yellow solid (ESI: m/z=1124 ($M^+$)).

Example 10: Synthesis of Mn Chelate 10a

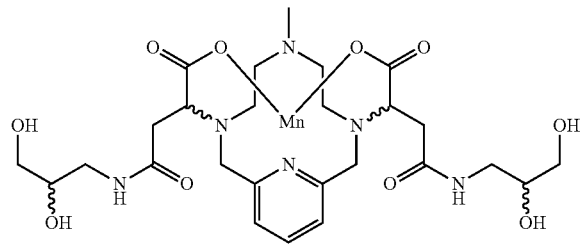

A 2-necked 50 mL round bottomed flask fitted with a magnetic stir bar was charged with Mn 2-arm C4 chelate (0.667 g, 1.32 mmol; obtained according to Example 8(ii)) and water (13.0 mL). 3-Amino-1,2-propanediol (0.253 g, 2.77 mmol) and the pH was adjusted to 7 with 1.0 M HCl. EDCl-HCl (0.599 g, 3.12 mmol) and HOBt hydrate (0.036 g, 0.266 mmol) were added and the pH was maintained at 6 with addition of 1.0 M HCl or 1.0 M NaOH as needed while stirring at ambient temperature for 7 h. A second aliquot of EDCl-HCl (0.610 g, 3.18 mmol) was added and the pH was maintained at 6 while stirring at ambient temperature for 17.5 h. A third aliquot of EDCl-HCl (0.610 g, 3.18 mmol) was added and the pH was maintained at 6 while stirring at ambient temperature for 70 h. The reaction solution was evaporated to dryness in vacuo and the crude product was purified on $C_{18}$ silica gel (100% water to 30% AcN in water) to give 0.160 g (19%) of the desired product as a pale yellow solid (ESI: m/z=652 ($M+H^+$)).

Example 11: Synthesis of Prior Art Mn Chelate

Example 11(i): Synthesis of Protected Mn 0-Arm Chelate

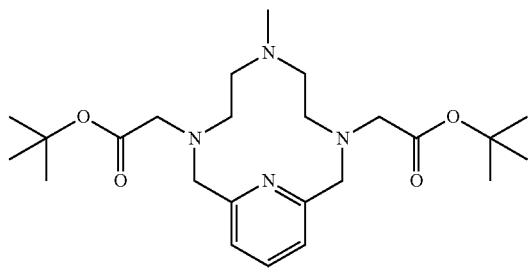 [SMILES: CN1CCN(CC(=O)OC(C)(C)C)Cc2cccc(n2)CN(CC(=O)OC(C)(C)C)CC1]

A 100 mL 3-necked round bottomed flask fitted with a magnetic stir bar and a reflux condenser was charged with protected cyclic 2-arm chelate (4.51 g, 8.53 mmol; obtained according to Example 2(ii)) and concentrated sulfuric acid (18.0 mL) and heated at 100° C. for 18 h. The reaction was cooled to ambient temperature and placed in an ice bath prior to adjusting the pH to 9.9 with 50% aqueous NaOH. The resulting suspension was transferred to a 250 mL 3-necked round bottomed flask and anhydrous potassium carbonate (11.78 g, 85.2 mmol) was added followed by AcN (25 mL) and t-butylbromoacetate (6.64 g, 34.0 mmol) and the reaction was heated at 70° C. for 3 h. The reaction was cooled to ambient temperature and the solids were removed via vacuum filtration. The filtrate was extracted with AcN (3×50 mL) and the organic layer was evaporated to dryness to give a dark brown oil which was purified on $C_{18}$ silica gel (100% water to 100% AcN in water) to give 1.28 g (33%) of the desired product as an off white solid. $^1$H NMR (400 MHz, $CD_3CN$, δ) 7.67 (1H, m), 7.12 (2H, m), 5.14 (2H, bs), 3.95 (4H, m), 3.44 (4H, m), 3.28 (6H, m), 3.16 (2H, m), 2.78 (3H, s), 1.42 (18H, s).

Example 11(ii): Synthesis of Deprotected Mn 0-Arm Chelate

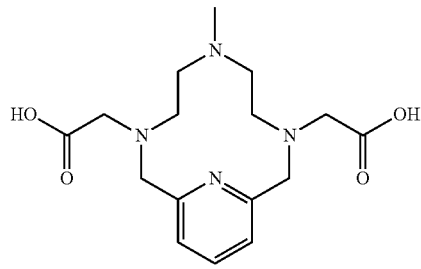 [SMILES: CN1CCN(CC(=O)O)Cc2cccc(n2)CN(CC(=O)O)CC1]

A 3-necked 100 mL round bottomed flask fitted with a magnetic stir bar and a reflux condenser was charged with protected Mn 0-arm chelate (1.28 g, 2.85 mmol), AcN (8.4 mL) and THF (21 mL). 88% aqueous formic acid (29.1 mL, 556 mmol) was added and the resulting solution was heated at 65° C. for 4 h. A second aliquot of 88% aqueous formic acid (29.1 mL, 556 mmol) was added and heating was continued for an additional 9 h. The solvent was removed in vacuo to leave a yellow oil which was used without further purification. $^1$H NMR (400 MHz, $CD_3OD$, δ) 7.74 (1H, m), 7.20 (2H, m), 4.07 (4H, m), 3.65 (4H, m), 2.91 (3H, s), 2.99 (4H, m), 1.92 (4H, m).

Example 1100: Synthesis of Prior Art Mn Chelate

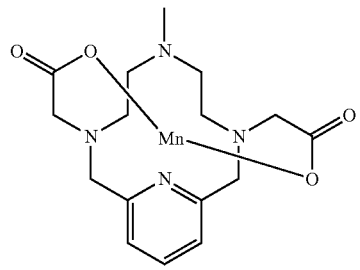

A 250 mL round bottomed flask fitted with a magnetic stir bar was charged with deprotected Mn 0-arm chelate (0.959 g, 2.85 mmol) and manganese(II) chloride tetrahydrate (1.119 g, 5.65 mmol). The pH was adjusted to 7.4 with 1.0 M NaOH and 1.0 M HCl as needed and the resulting solution was stirred at ambient temperature for 15.5 h. The pH was then adjusted to 10 with saturated aqueous sodium carbonate and the resulting off-white precipitate was removed via vacuum filtration. The filtrate was concentrated to dryness in vacuo and purified on $C_{18}$ silica gel (100% water to 10% AcN in water) to give 0.511 g (46% over 2 steps) of the desired product as a pale yellow solid (ESL m/z=390 ($M^+$)).

Example 12: In Vivo $^{54}$Mn Biodistribution Studies in Rats $^{54}$Mn labeled chelates for biodistribution studies were prepared using the following method. To a 3 mL glass vial fitted with a magnetic stir bar was added the respective manganese containing chelate (1 mg) and 1.0 M ammonium formate, pH=4 (0.5 mL) (pH=5 for prior art Mn Chelate). $^{54}MnCl_2$ in 1.0 M HCl (~500 μCi) was then added and the resulting solution was heated at 40° C. for 16 h. The resulting solution was purified via preparative HPLC to remove unchelated Mn. The radioactive fraction was collected and evaporated to dryness in vacuo. The radioactive residue was taken up in water containing non-radioactive Mn chelate (0.310 M) such that ~30 μCi of radioactivity was formulated in a dose of 0.620 mmol Mn/kg with an injection volume of 2 mL/kg.

The experimental protocol conformed to the Guide for the Care and Use of Laboratory Animals and was approved by the IACUC at General Electric Global Research (Niskayuna, NY). Female Sprague-Dawley rats (130-150 g; Charles River Laboratories; Massachusetts; USA) were housed in standard cages, provided with ad libitum access to standard commercial food and water, and were maintained on an alternating 12-hr light-dark cycle in rooms with controlled temperature and humidity. Prior to injection of $^{54}$Mn labelled chelates, rats were anesthetized via inhaled 3% Isoflurane (Piramal, NDC 66794-013-25; EZ-Anesthesia EZ700 Isoflurane Vaporizer, S/N 107). The injection site was prepped with alcohol wipes and a temporary 27 Ga catheter (Surflo SROX2419V) was placed in a tail vein. 30 μCi (0.74 MBq) of $^{54}$Mn labelled chelate formulated with respective non-radioactive Mn(II) based chelate was dosed at 0.620 mmol non-radioactive Mn chelate/kg at an injection volume of 2 m L/kg was injected at a rate of 1 mL/min. Following injection animals were individually housed in wire bottom cages lined with filter paper until first urine void was collected. The rats were then cohoused in standard long term caging. 7 days post injection, the animals were sacrificed by $CO_2$ immersion and organs and tissues of interest were removed and assayed for radioactivity using a Wizard 2480 gamma counter (Perkin Elmer, Beaconsfield, UK).

Naïve rats (Charles River Laboratories; Massachusetts; USA) received a single dose of 0.620 mmol/kg (approximately 30 μCi, 0.740 MBq) of test item via tail vein by injection. Additionally, one group of animals received osmolality matched saline (concentrated NaCl for injection: APP Pharmaceuticals part #NDC 63323-187-30 Lot #6008656 mixed with Sterile Water for Injection: Hospira part #NDC 0409-7990-09 Lot #49-396-DKas) as negative control (Table 1). After sacrifice, the organs and tissues were removed and assayed for residual radioactivity (i.e. $^{54}$Mn organ retention) 7 days post single administration.

TABLE 1

Study design for the $^{54}$Mn Biodistribution study in rats. Test item: Prior Art Mn Chelate; Mn Chelate 3 and Mn Chelate 4. Residual radioactivity (% ID) was assessed 7 days following single iv administration.

| Group number | Test item | Number of animals/sex | Radioactive dose (μCi) | Chemical dose (mmol/kg) | In life time |
|---|---|---|---|---|---|
| 1 | [$^{54}$Mn] Prior Art Mn Chelate[1] | 4/F | 30 | 0.620 | 7 day |
| 2 | [$^{54}$Mn] Mn Chelate 3 | 4/F | 30 | 0.620 | 7 days |
| 3 | [$^{54}$Mn] Mn Chelate 4 | 4/F | 30 | 0.620 | 7 day |
| 4 | Saline | 4/F | 0 | 0 | 7 day |

The aim of this study was to evaluate the tissue distribution in naïve rats 7 days after a single injection of Mn(II) based chelates labelled with $^{54}$Mn (radioactive isotope). Residual radioactivity (e.g., % ID) was measured in the relevant collected tissues (Table 2). The Mn(II) based chelates evaluated showed levels of $^{54}$Mn retention within physiological manganese level variability in almost all organs and tissues collected, and trace amounts were present in the excretory organs. Detection of $^{54}$Mn in the liver and kidney was expected for all compounds evaluated as those organs are part of the primary route of excretion for all MR contrast agents. The Mn(II) based chelates demonstrated reduced distribution to the heart and the brain compared to literature data with $^{54}$MnCl$_2$. Indeed, the lower levels (e.g., within endogenous level variability) of $^{54}$Mn detected in the brain for the Mn Chelate 3 and Mn Chelate 4 are of great interest because brain is one of the toxicity target organ for Mn(II). Surprisingly, the lower levels $^{54}$Mn in the tibia/fibula and femur for Mn Chelate 3 and 4 are also indicative of improved in vivo stability of this class of compounds when compared to the prior art Mn Chelate considering the bones act as a reservoir of free metal ions (e.g., Mn(II)). The biodistribution profiles of the three Mn(II) based chelates demonstrated the in vivo stability of the paramagnetic complexes is a property can be modulated by the structural design of the chelate moiety with Mn Chelate 3 and Mn Chelate 4 showing an improved stability compared to the prior art Mn Chelate.

TABLE 2

% ID ± standard deviation for collected tissues. Retained activity has been measured 7 days post single administration of 0.62 mmol non-radioactive Mn chelate/kg dose containing ~30 µCi of $^{54}$Mn labelled chelate.

| Tissue | Prior Art Mn Chelate[a] | Mn Chelate 4[b] | Mn Chelate 3[c] |
|---|---|---|---|
| Brain | 0.007 ± 0.002% | 0.003 ± 0.000% | LOD |
| Pituitary Gland | ≤LOD | ≤LOD | N.M. |
| Olfactory Bulb | ≤LOD | ≤LOD | ≤LOD |
| Liver | 0.072 ± 0.017% | 0.075 ± 0.011% | 0.091 ± 0.017% |
| Kidney | 0.012 ± 0.002% | 0.038 ± 0.017% | 0.026 ± 0.005% |
| Spleen | ≤LOD | ≤LOD | ≤LOD |
| Bladder | ≤LOD | ≤LOD | ≤LOD |
| Heart | ≤LOD | ≤LOD | ≤LOD |
| Lungs | ≤LOD | ≤LOD | ≤LOD |
| Muscle | ≤LOD | ≤LOD | ≤LOD |
| Skin | ≤LOD | ≤LOD | ≤LOD |
| Blood | ≤LOD | ≤LOD | ≤LOD |
| Tibia/Fibula | 0.002 ± 0.000% | ≤LOD | ≤LOD |
| Femur | 0.003 ± 0.001% | ≤LOD | N.M. |

[a]LoD = 0.002% ID, n = 8;
[b]LoD = 0.002% ID, n = 8;
[c]LoD = 0.005% ID, n = 3

Example 13: Water Solubility of Mn(II) Based Chelates

The solubility of Mn(II) based chelates was confirmed by dissolving purified Mn(II) based chelates (~99% purity) in a prescribed volume of solvent (Millipore water 18.2 Mega-Ohm from a Millipore BioCell Benchtop unit) to provide a solution of given volume. Solutions were visually inspected for homogeneity and filtered through a 0.45 um PTFE filter membrane if necessary. The assessment was carried out at 25° C. Final sample concentrations were confirmed by determination of final Mn(II) concentration via ICP-MS (Spectro Arcos FHS12, S/N 10003910 or S/N 12006120).

The size of the paramagnetic complex can affect the water solubility hence the distribution into the extracellular space and clearance rate from the body. An adequate water solubility is also required to maintain low the volume of injection to facilitate the administration of the contrast agents to patients. To this end, typically commercially available Gd(III) contrast agents are formulated at a concentration of 0.5 M. The solubility of the Mn(II) based chelates were confirmed within standard solubility range (>0.5 M) independently from the increased molecular size observed for some compounds (Table 3).

TABLE 3

MW and solubility range for exemplary Mn(II) based chelates comprised in this invention. Solubility was assessed at 25° C.

| Compound | MW (g/mol) | Solubility in water at 25° C. (M) |
|---|---|---|
| Prior Art Mn Chelate | 389.31 | >0.5 |
| Mn Chelate 3 | 1137.09 | >0.5 |
| Mn Chelate 4 | 887.3 | >0.5 |
| Mn Chelate 5 | 859.78 | >0.5 |
| Mn Chelate 7 | 1152.07 | >0.5 |
| Mn Chelate 9 | 707.67 | >0.5 |
| Mn Chelate 10 | 679.62 | >0.5 |
| Mn Chelate 5a | 831.72 | >0.5 |
| Mn Chelate 10a | 651.57 | >0.5 |

Example 14: In Vitro Proton Relaxivity and Nuclear Magnetic Relaxation Dispersion (NMRD) Profiles of Mn(II) Based Chelates Both the longitudinal and transverse relaxation times were measured in human serum (BioreclamationIVT, Cat #HMSRM-M) to reflect the efficiency of the Mn(II) based chelates in an environment close to physiological. The relaxivity assessment was carried out at a concentration ranging from 5 to 0 mM Mn(II), at 40° C. using a Minispec Mq benchtop NMR relaxometer (Bruker Instruments, Rheinstetten, Germany) operating at 60 MHz (1.4 T) with an inversion recovery pulse sequence. The longitudinal and transverse relaxivities of the complexes (e.g., $r_1$ and $r_2$ respectively) were calculated by plotting the reciprocal of their relaxation time versus the manganese concentration as determined via ICP-MS (Spectro Arcos FHS12, S/N 10003910 or S/N 12006120) for each Mn(II) based chelates. The dependence of $T_1$ by $B_0$ (i.e., magnetic field) applied was assessed via the acquisition of $^1$H Nuclear Magnetic Relaxation Dispersion (NMRD) profiles. A dedicated Stelar SMARTracer Fast Field Cycling relaxometer (0.01-10 MHz) and a Bruker WP80 NMR electromagnet adapted to variable field measurements (20-80 MHz) and controlled by a SMARTracer PC-NMR console was used to record the $^1$H NMRD profiles over an extended range of Larmor Frequencies (from 0.01 to 80 MHz). The temperature was monitored by a VTC91 temperature control unit and maintained by a gas flow. The temperature was determined by previous calibration with a Pt resistance temperature probe. High field relaxivities were measured on a Bruker AVANCE NMR spectrometer at 400 MHz. A total of 25 data points per NMRD profile were recorded at each temperature, pH 6.9 and with a manganese concentration in the samples of 6.99, 6.78 and 4.45 mM for the prior art Mn Chelate, Mn Chelate 4 and Mn Chelate 3, respectively. The concentration of Mn(II) in all samples was verified by Bulk Magnetic Susceptibility (BMS) measurements. Relaxivity was computed by subtracting the relaxation rate of the medium (distilled water) from the relaxation rate of the Mn(II) complex solution at each field strength and dividing the difference by the manganese concentration verified by BMS measurements.

The linear fit (R2>0.99 for all compounds examined) of $1/T_1$ and $1/T_2$ as a function of Mn concentration generated the $r_1$ or $r_2$ values reported in Table 4 for human serum.

TABLE 4

Relaxivities $r_1$ and $r_2$ in human serum at 60 MHz and 40° C. for exemplary Mn(II) based chelates.

| Compound | $r_1$ (mM$^{-1}$s$^{-1}$) | $r_2$ (mM$^{-1}$s$^{-1}$) |
|---|---|---|
| Prior Art Mn Chelate | 3.0 | 7.4 |
| Mn Chelate 3 | 8.0 | 18.3 |
| Mn Chelate 4 | 5.3 | 13.7 |
| Mn Chelate 5 | 5.2 | 13.1 |
| Mn Chelate 7 | 6.0 | 12.8 |
| Mn Chelate 9 | 4.3 | 12.0 |
| Mn Chelate 10 | 4.3 | 11.6 |
| Mn Chelate 11 | 4.6 | 12.3 |
| Mn Chelate 5a | 3.7 | 7.9 |
| Mn Chelate 10a | 3.8 | 8.8 |

The relaxivity measurements demonstrated all Mn(II) based chelates are viable and within the standard relaxivity (i.e., $r_1$ and $r_2$) ranges of commercially-available MRI contrast agents ($r_1 \geq 3$ mM$^{-1}$ s$^{-1}$). Of specific interest is the $r_1$ (i.e., longitudinal relaxivity) value of the Mn(II) based chelates which represents the ability of the chelates to generate $T_1$ (or positive) contrast in vivo following iv administration. Whereas, the $r_2$ (i.e., transverse relaxivity) value represents the ability of the Mn(II) based chelates to generate $T_2$ (or negative) contrast following iv administration.

Figure 2:
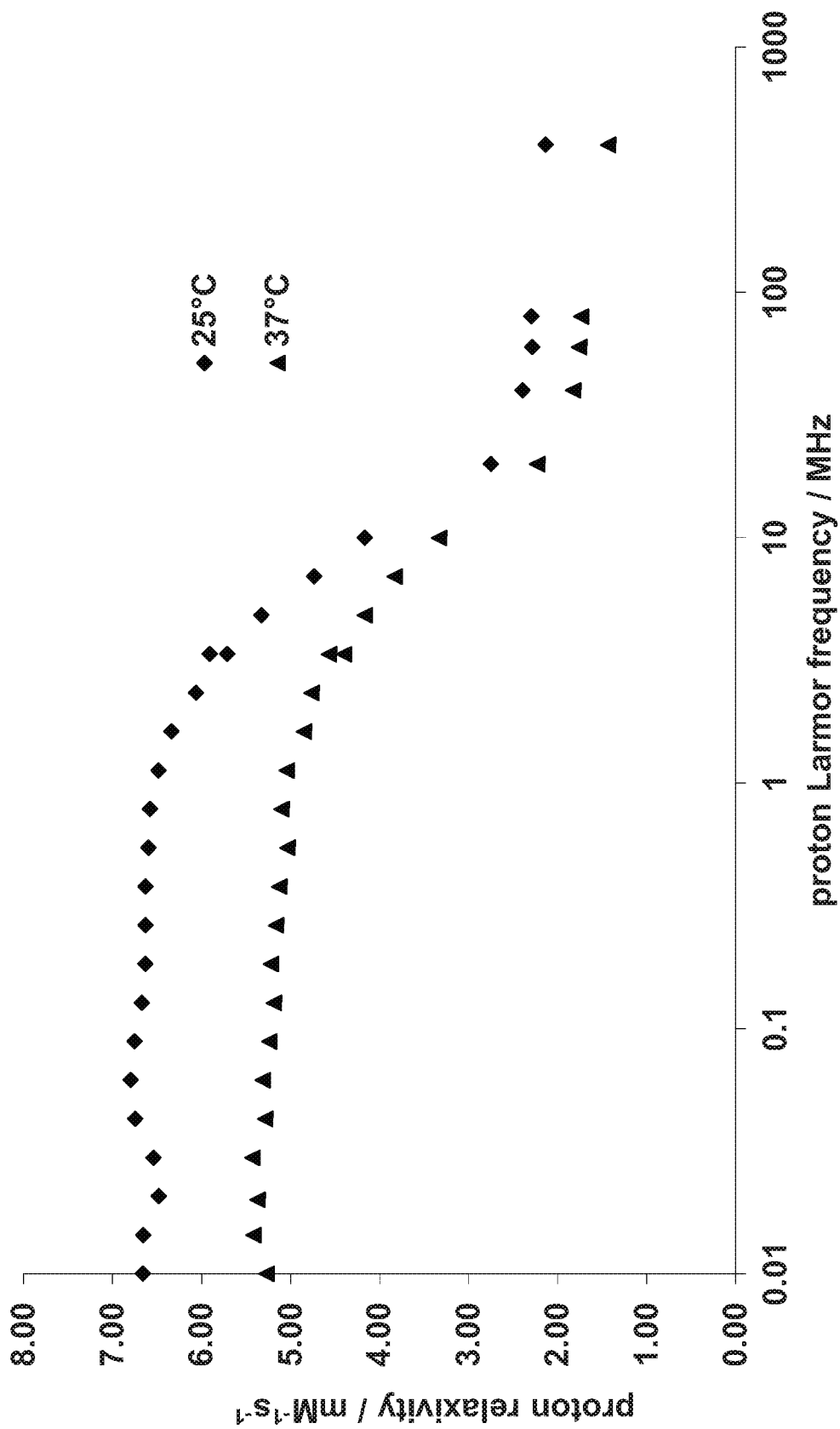
FIGS. 2 and 3 show $^1H$ NMRD profiles recorded for Mn(II) based chelates as measured by the method described in Example 14.
Figure 3:
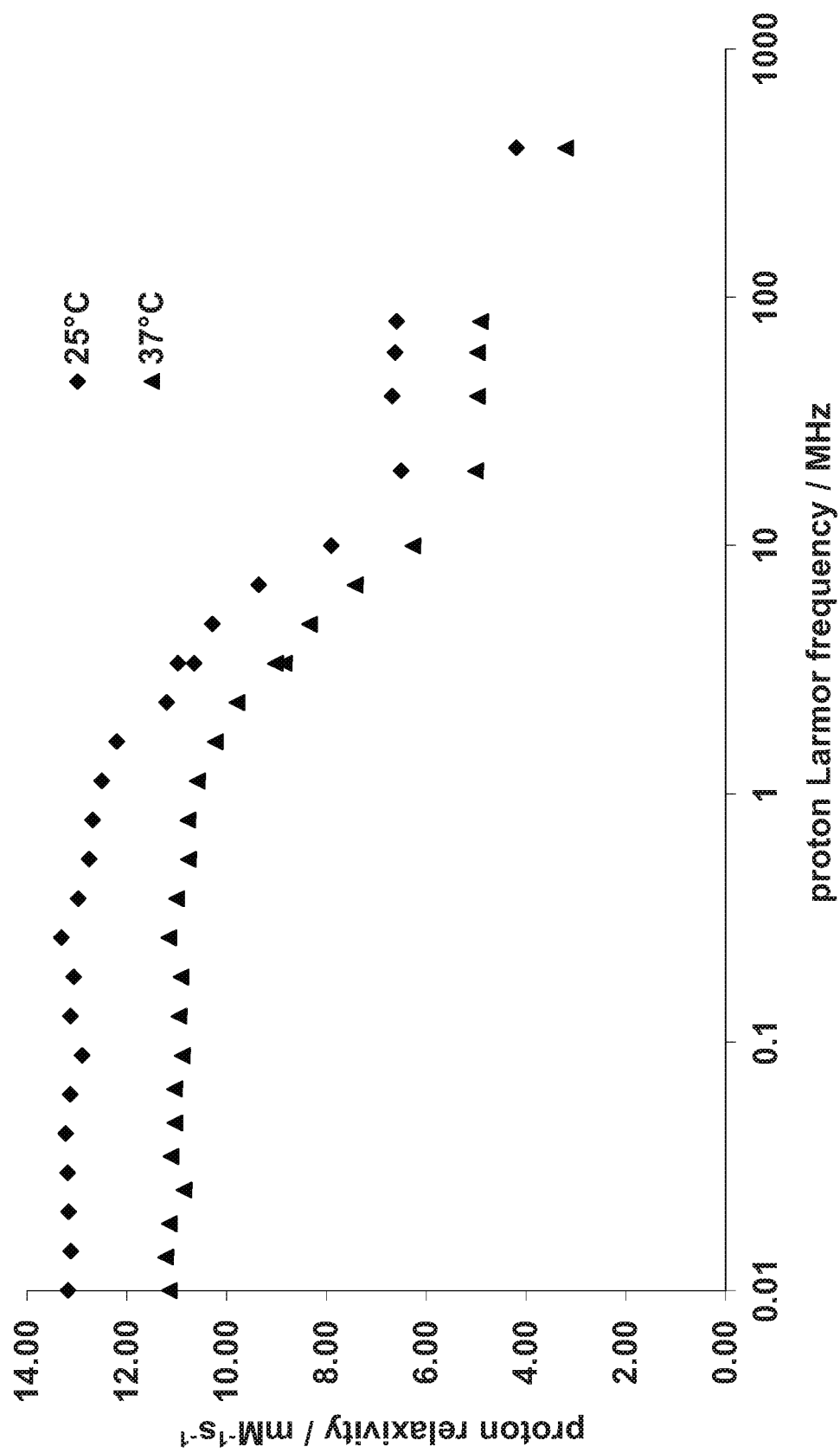

$^1$H NMRD profiles were recorded for the prior art Mn Chelate and Mn Chelate 4 (FIG. 2 and FIG. 3, respectively). Both Mn(II) based chelates evaluated demonstrated a viable $^1$H NMRD profile with lower longitudinal relaxivities than the Mn(II) aqua ion and only one dispersion in the profile around 1 MHz. The NMRD profile of Mn Chelate 4 (FIG. 3) showed a small $r_1$ hump in the frequency region between 60 and 80 MHz (~1.5 T) which may be advantageous for future clinical imaging application with an improved efficiency of the Mn(II) based chelate at clinically relevant magnetic field strength. This high field $r_1$ hump is due to a small decrease in the tumbling rate related to the larger molecular size of the compound.

Example 15: Dissociation Kinetics of Mn(II) Based Chelates

Kinetic inertness was evaluated at slightly acidic pH due to the slow rate of dissociation of the paramagnetic complex at physiological pH and to the potential hydrolysis of the metal ions at the concentrations used for the experiments and at pH values close to physiological.

$Zn^{2+}$ Exchange

The dissociation kinetics of Mn(II) based chelates (concentration 1 mM) of the invention was assessed via $Zn^{2+}$ transmetallation recording the time-dependent variation of the longitudinal relaxation time (i.e., $T_1$). The assessment was completed in a set of experiments including for the prior art Mn Chelate different concentrations of competing metal ion (5, 10, 20, 40 equivalents of $Zn^{2+}$); at 25° C. and different pH (pH: 5.1; 5.4; 5.7). The dissociation kinetics for Mn Chelate 4 (concentration 1 mM) was assessed in the presence of 5 eq of $Zn^{2+}$ at 25° C. and pH 5.1 and 5.7. For both assessments, the reaction mixture contained 0.15 M NaCl and 50 mM N-methyl piperazin buffer (i.e., NMP).

The longitudinal relaxation time changes were monitored at 1 MHz for the prior art Mn Chelate and at 0.01 MHz for Mn Chelate 4. Indeed, the release of the free Mn$^{2+}$ ion induced by Zn$^{2+}$ leads to a decrease of the relaxation time for both Mn(II) based chelates evaluated in all experimental conditions. The acquisition frequencies for this set of experiments have been selected based on the difference between the observed relaxivity of the Mn(II) aqua ion and the Mn(II) based chelates (e.g., prior art Mn Chelate and Mn Chelate 4) in order to have enough differentiation between the two chemical species. The frequencies have been selected based on the $^1$H NMRD profiles as displayed in FIG. 1 for prior art Mn Chelate, Mn Chelate 4 and MnCl$_2$.

$Cu^{2+}$ Exchange

The dissociation kinetics of the prior art Mn Chelate, Mn Chelate 4 and Mn Chelate 3 at a concentration of 0.2 mM was assessed via Cu$^{2+}$ transmetallation recording the time-dependent change of the UV-Vis absorbance in the presence of an excess of competing metal ion (10 and 40 equivalents of Cu$^{2+}$); at 25° C. and different pH (pH: 5.0; 5.2; 5.4). For all assessments, the reaction mixture contained 0.15 M NaCl; 50 mM NMP. The λ for the acquisition of the UV-Vis spectra was selected based on the difference between the observed absorbance for the Mn(II) based chelates (e.g., prior art Mn Chelate, Mn Chelate 3 and Mn Chelate 4) and the newly formed Cu$^{2+}$-complex in order to have the best differentiation between the two chemical species. The UV-Vis spectra were acquired at λ=300 nm on a Perkin-Elmer Lambda 19 spectrophotometer. Indeed, the displacement of Mn(II) ion induced by Cu$^{2+}$ led to an increase of the observed absorbance at λ=300 nm for all Mn(II) based chelates in all experimental conditions. This increase is due the formation of the Cu$^{2+}$-complex.

Results of Transmetallation Experiments

Figure 4:
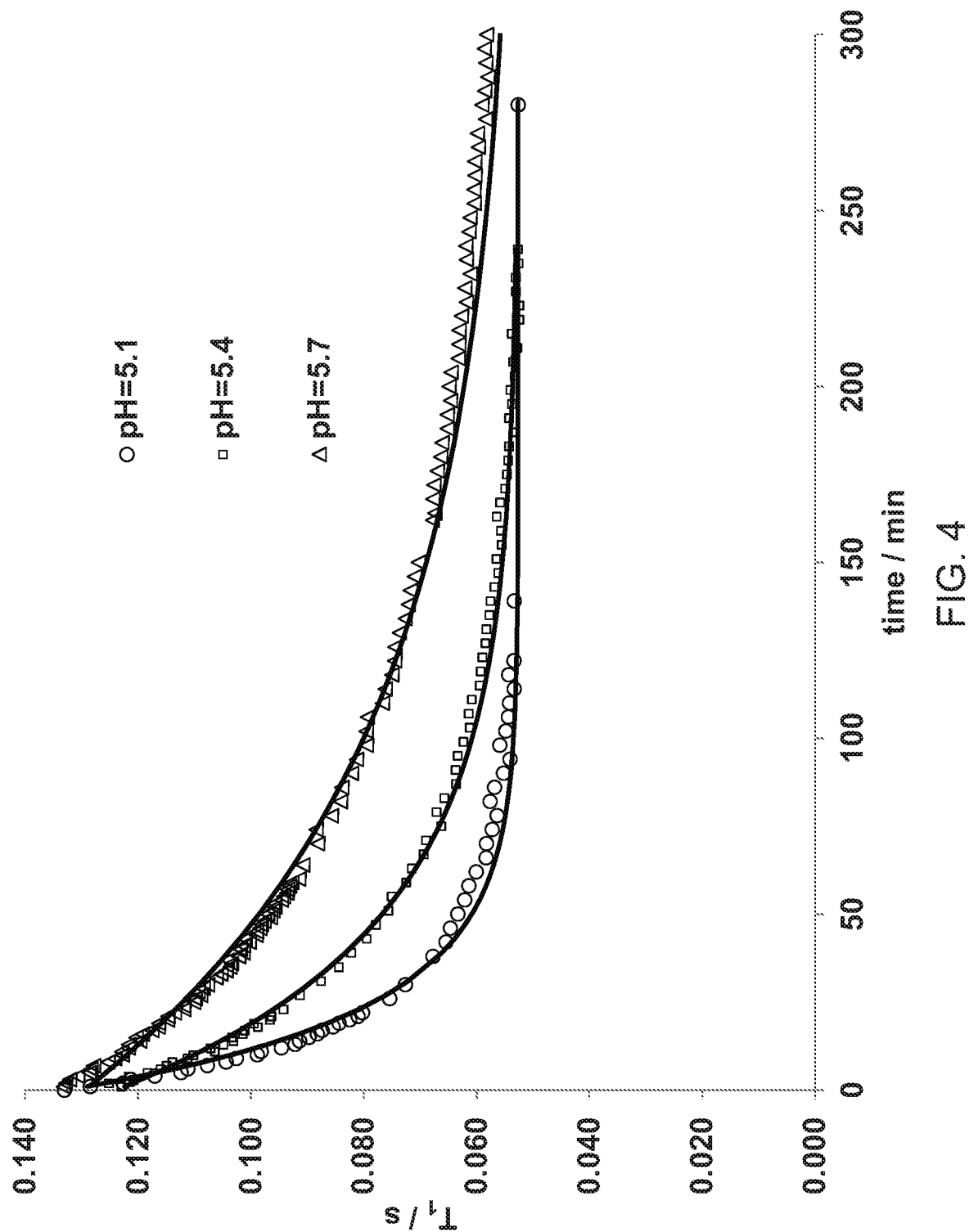
FIGS. 4 and 5 illustrate the results of the transmetallation experiments carried out for a prior art Mn chelate compound as described in Example 15.
Figure 5:
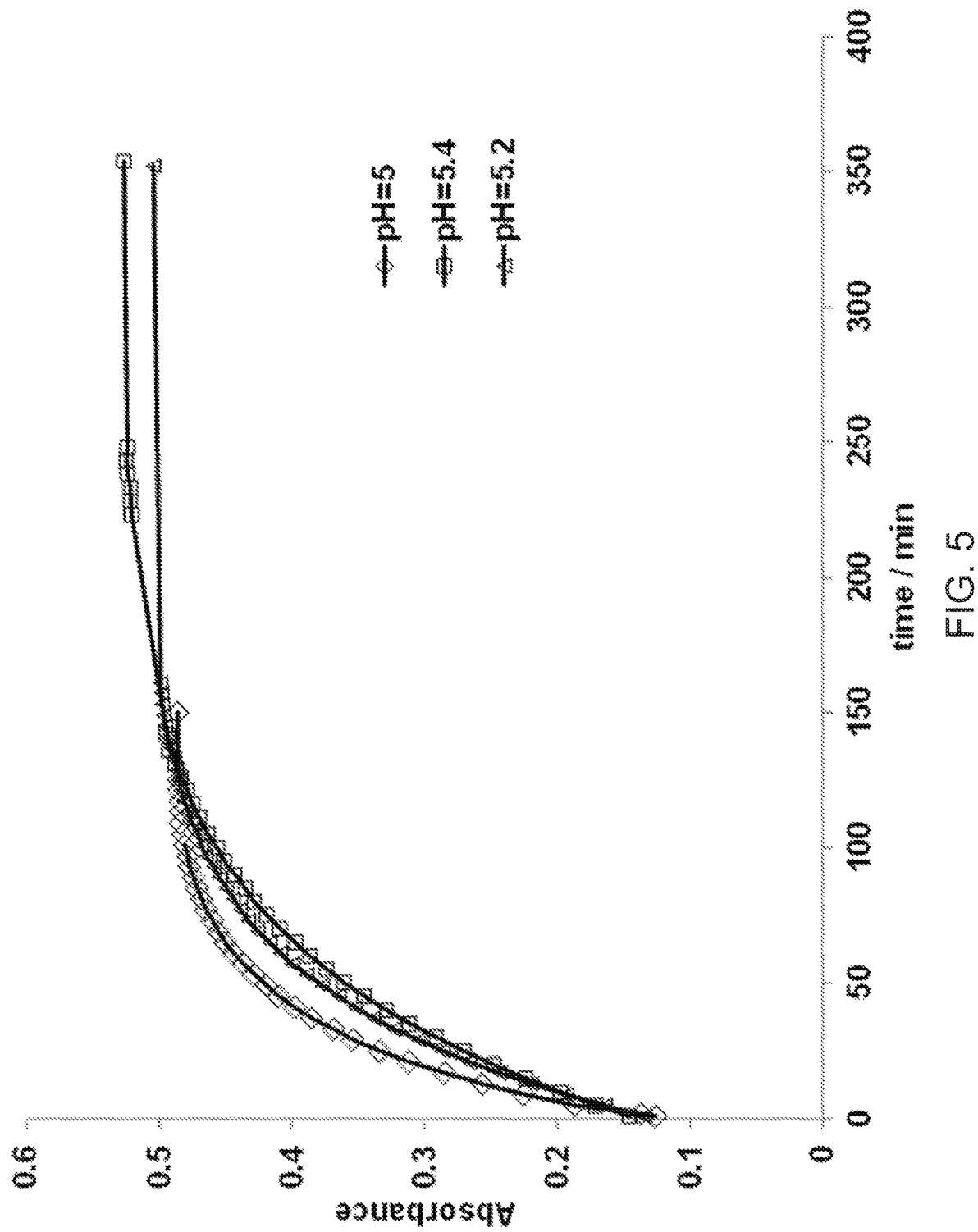

Zn$^{2+}$ and Cu$^{2+}$ transmetallation were studied by using an excess of the exchanging metal ion to demonstrate kinetic inertness of Mn(II) based chelates. For any of the transmetallation experiments carried out with the prior art Mn Chelate (e.g., at different pH; different Zn$^{2+}$ or Cu$^{2+}$ concentration) it was evident that the variation of the relaxation rate $T_1$ (for the Zn$^{2+}$-exchange; FIG. 4) or the variation of the UV-Vis absorbance (for the Cu$^{2+}$-exchange; FIG. 5) caused by competing metal ion was a "single phase" process better described as a mono-exponential function. Indeed, the prior art Mn Chelate showed an exchange reaction governed by a pseudo-first order equation (1) with the reaction rate directly proportional to the total concentration of Mn(II) based chelates. The rate of dissociation described by $k_{obs}$ was calculated via equation (1) where $[MnL]_{tot}$ is the total concentration of Mn(II) based chelates and t is the observation time.

$$-\frac{d[MnL]_{tot}}{dt} = k_{obs}[MnL]_{tot} \quad \text{(Equation 1)}$$

Figure 6:
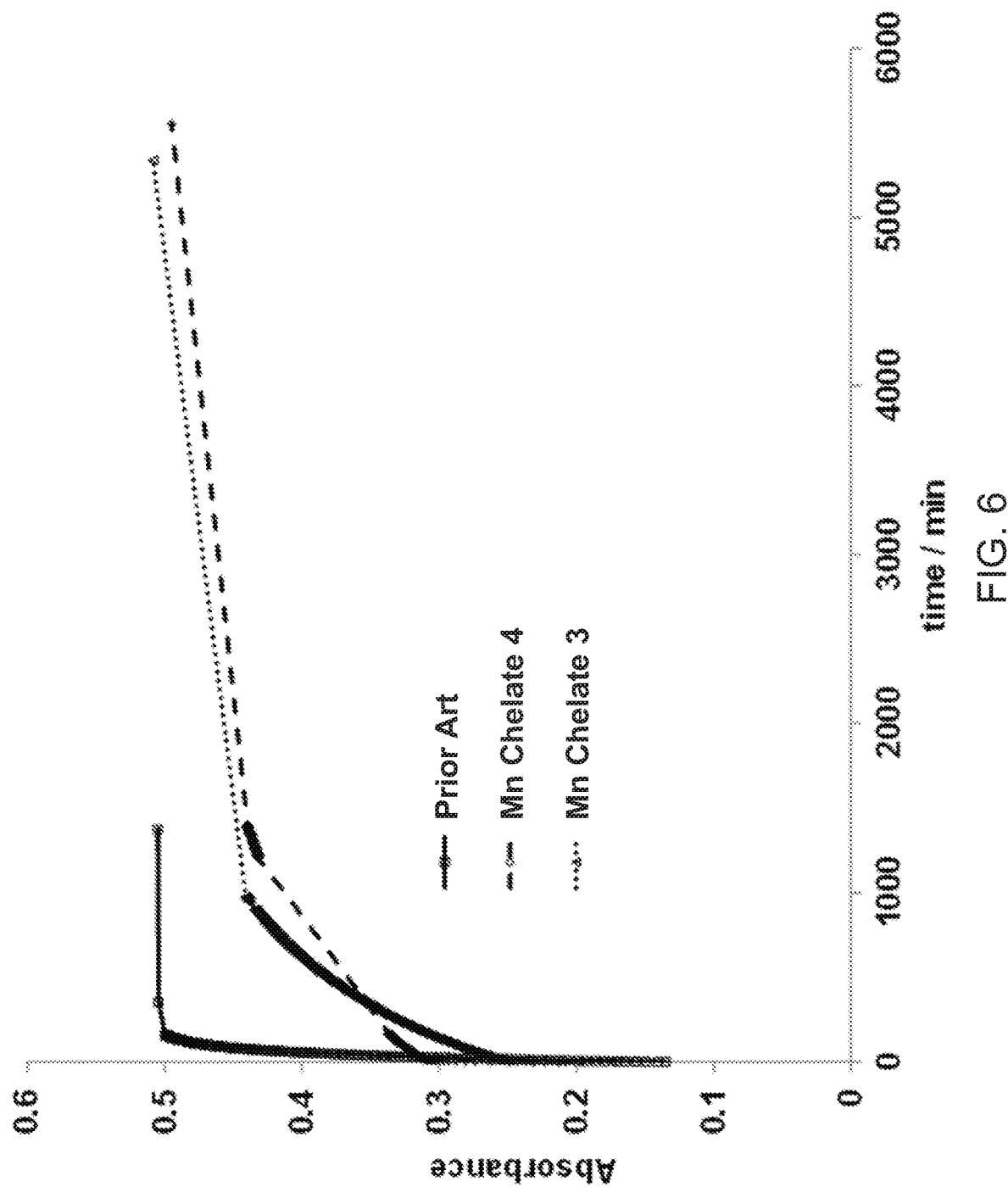
FIGS. 6 and 7 shows a comparison of the transmetallation results obtained for a prior art compound and for certain compounds of the invention as described in Example 15.
Figure 7:
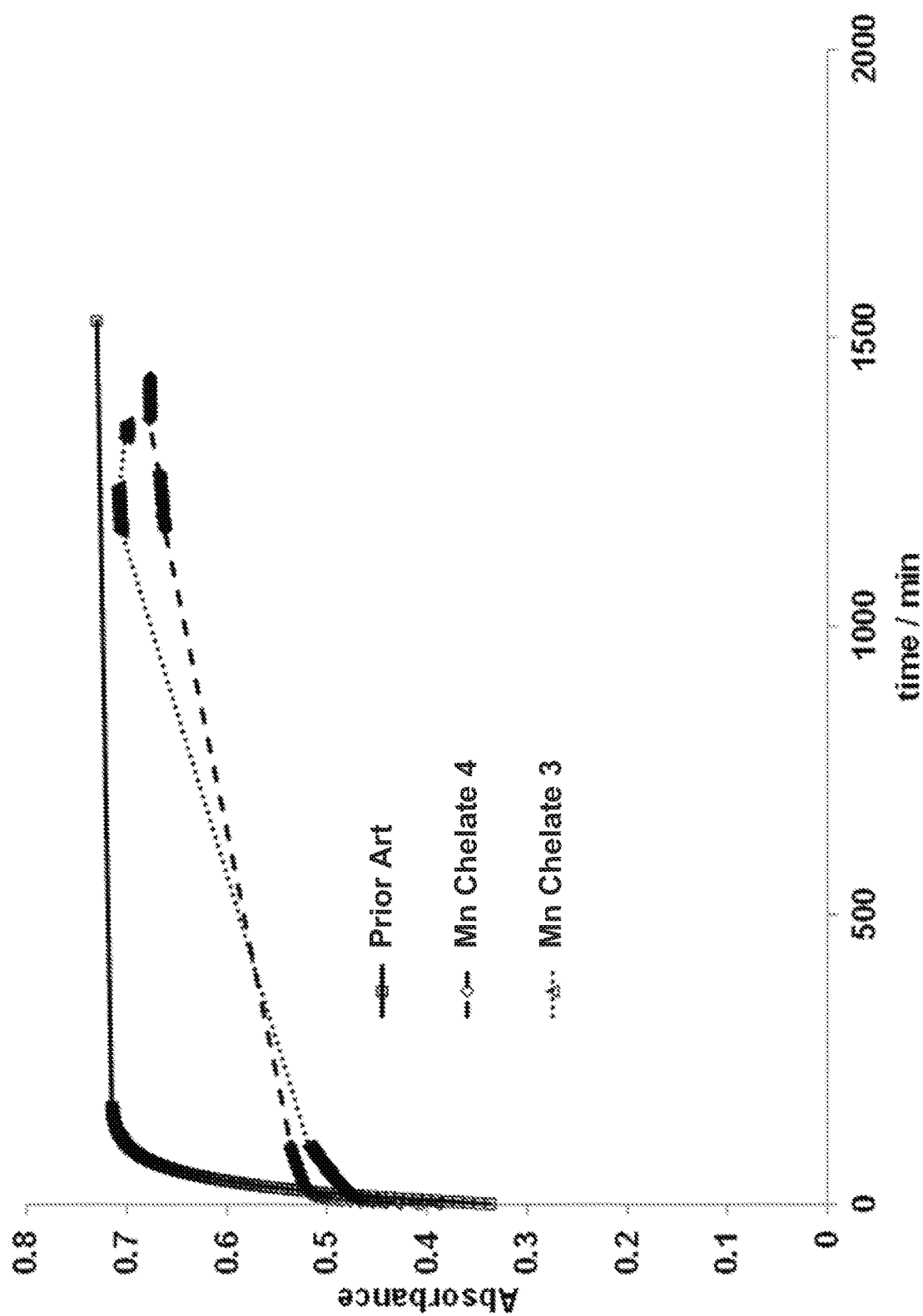

In contrast to the prior art Mn Chelate, for Mn Chelate 4 and Mn Chelate 3 the time dependent curves of the UV-Vis absorption in the transmetallation reaction with Cu$^{2+}$ were not described by a monoexponential function, but showed a biphasic nature (i.e., two steps-mechanisms dissociation process). The biphasic nature of the of the Mn(II)—Cu$^{2+}$ exchange process was evident and confirmed for Mn Chelate 3 and Mn Chelate 4 at all pH and competing metal ion concentrations assessed. The comparison between the kinetic curves for the prior art Mn chelate, Mn Chelate 3 and Mn Chelate 4 describing the transmetallation with $Cu^{2+}$ at different pH are presented in FIG. 6 and FIG. 7. The curves profile clearly demonstrated the different dissociation mechanism of the three compounds when examined in the same experimental conditions.

Figure 8:
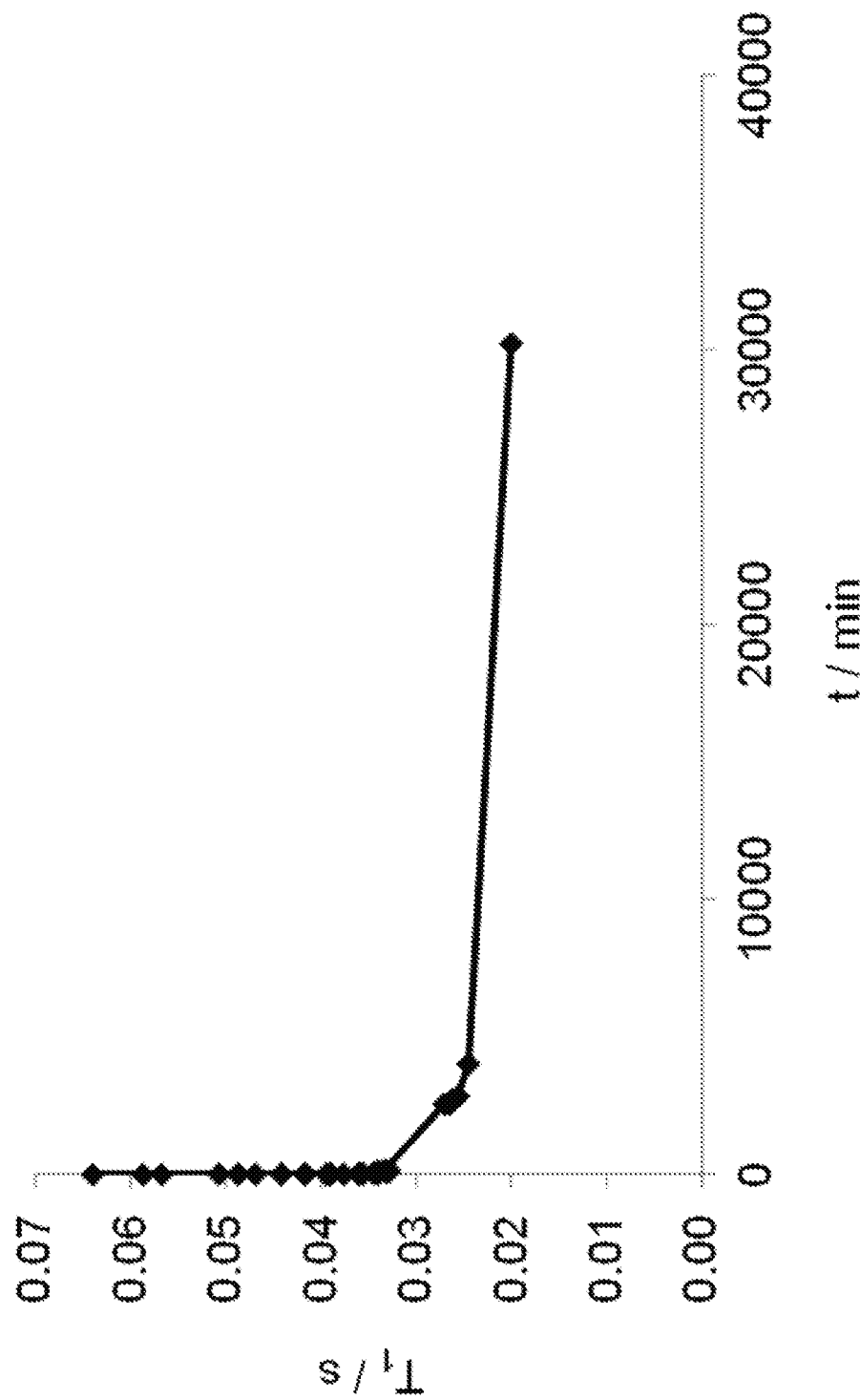
FIG. 8 shows the time dependent curve of the longitudinal relaxation time (i.e., T1) for a compound of the invention.

To confirm the biphasic nature of the kinetic dissociation curves for Mn Chelate 3 and Mn Chelate 4 the transmetallation reaction with $Zn^{2+}$ was assessed for Mn Chelate 4. The time dependent curves of the longitudinal relaxation time (i.e., $T_1$) were recorded at pH 5.1 and 5.7 (FIG. 8) and they confirmed the biphasic behaviour of the kinetic curves hence of the dissociation process for Mn Chelate 4.

Mn Chelate 3 and Mn Chelate 4 showed an exchange reaction governed by the sum of two independent exponential functions. These biphasic kinetic curves could be mathematically well fitted with the biexponential equation (2) where A is the observed absorbance; b, $A_1$ and $A_2$ are constants specific for the biphasic dissociation process for a Mn(II) based chelate; $k_{obs1}$ and $k_{obs2}$ are the rate constants describing the biphasic dissociation and t is the observation time.

$$A = b - A_1 e^{-k_{obs1} t} - A_2 e^{-k_{obs2} t} \qquad \text{(Equation 2)}$$

The rates of the biphasic dissociation for Mn Chelate 3 and Mn Chelate 4 described by $k_{obs1}$ and $k_{obs2}$ and of the monophasic dissociation for the prior art Mn Chelate described by $k_{obs}$ were calculated via equation (2) and (1) respectively for the different experimental conditions utilized in the set of experiments.

TABLE 5

Observed rate constants $k_{obs1}$ and $k_{obs2}$ calculated by a monoexponential (for the prior art Mn Chelate) or biexponential equations (for Mn Chelate 3 and Mn Chelate 4) for $Cu^{2+}$ transmetallation.

| | Prior Art Mn Chelate | Mn Chelate 4 | | Mn Chelate 3 | |
|---|---|---|---|---|---|
| $C_{Cu2+}$ (M) | $k_{obs1}$ (min$^{-1}$) | $k_{obs1}$ (min$^{-1}$) | $k_{obs2}$ (min$^{-1}$) | $k_{obs1}$ (min$^{-1}$) | $k_{obs2}$ (min$^{-1}$) |
| pH = 5.4  0.002 | 0.017 | 0.201 | 0.001 | | |
| pH = 5.2  0.002 | 0.022 | 0.240 | 0.0009 | 0.303 | 0.0015 |
| pH = 5.0  0.002 | 0.034 | 0.340 | 0.0013 | 0.483 | 0.0023 |
| 0.004 | 0.032 | | | | |
| 0.008 | 0.035 | 0.190 | 0.0009 | 0.378 | 0.0024 |

From the qualitative comparison of the kinetic curves and preliminary $k_{obs}$ it was evident that Mn Chelate 3 and Mn Chelate 4 dissociate with a different mechanism described by a biexponential function and at a slower rate compared to the prior art Mn Chelate. To quantitatively compare the kinetic inertness of these Mn(II) based chelates, the direct comparison of the evolution of the UV-Vis absorbance at 300 nm was recorded for the $Cu^{2+}$ exchange reaction. Direct comparison of the UV-Vis absorbance allowed quantification of the conversion of the Mn(II) based chelates into $Cu^{2+}$ based chelates during the transmetallation reaction which can be correlated to the kinetic inertness of the Mn(II) complex. The "conversion" was calculated following equation (3), where $A_t$ is the absorbance at a time t (or end of the reaction), $A_0$ is the absorbance at time zero (or beginning of the acquisition) and $A_{eq}$ is the absorbance at the equilibrium.

$$\text{Conversion} = \frac{A_t - A_0}{A_{eq} - A_0} \qquad \text{(Equation 3)}$$

Figure 9:
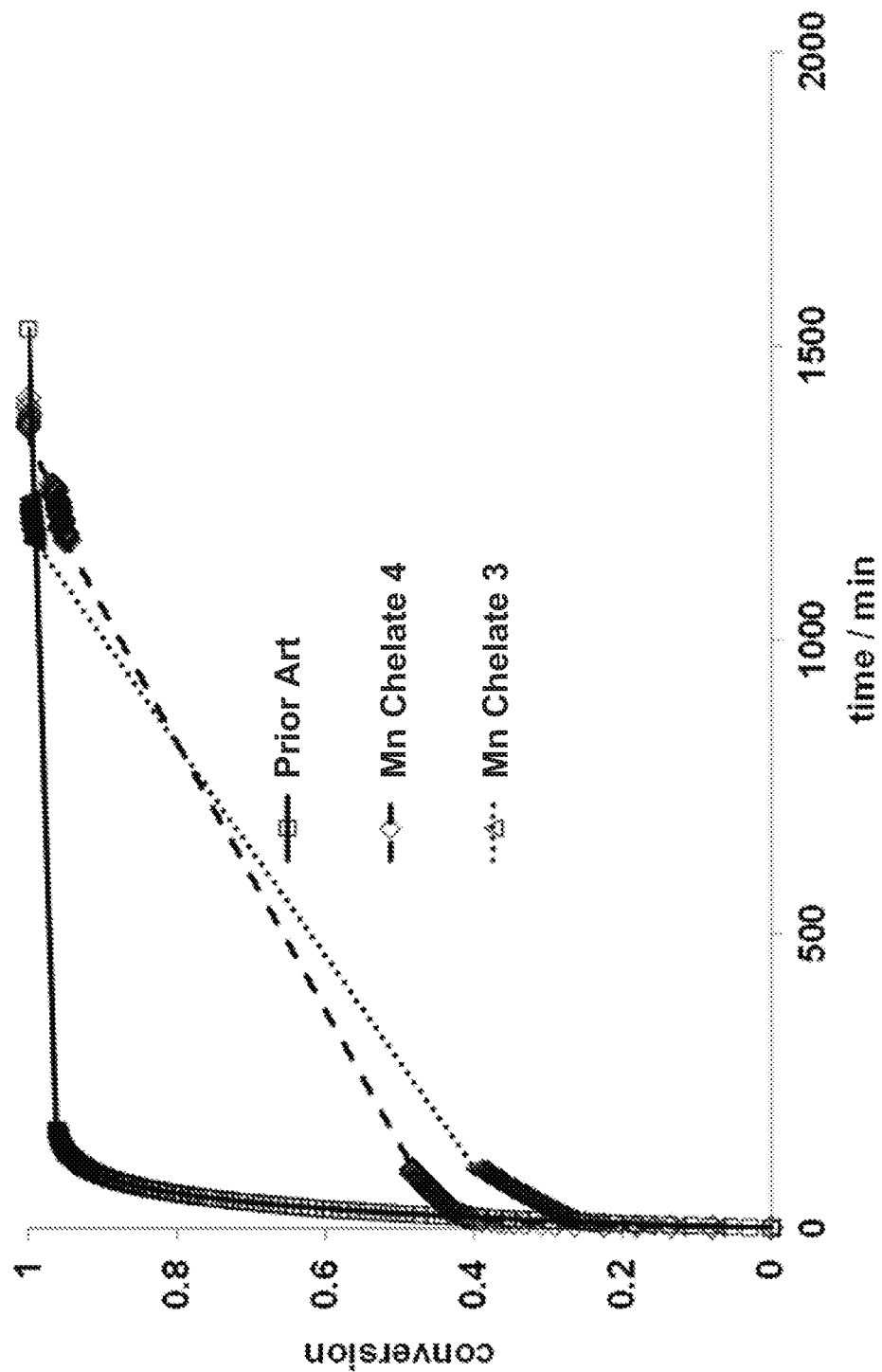
FIGS. 9 and 10 illustrate the conversion caused by competing $Cu^{2+}$ with Mn chelate compounds of the invention compared with a prior art Mn chelate compound.
Figure 10:
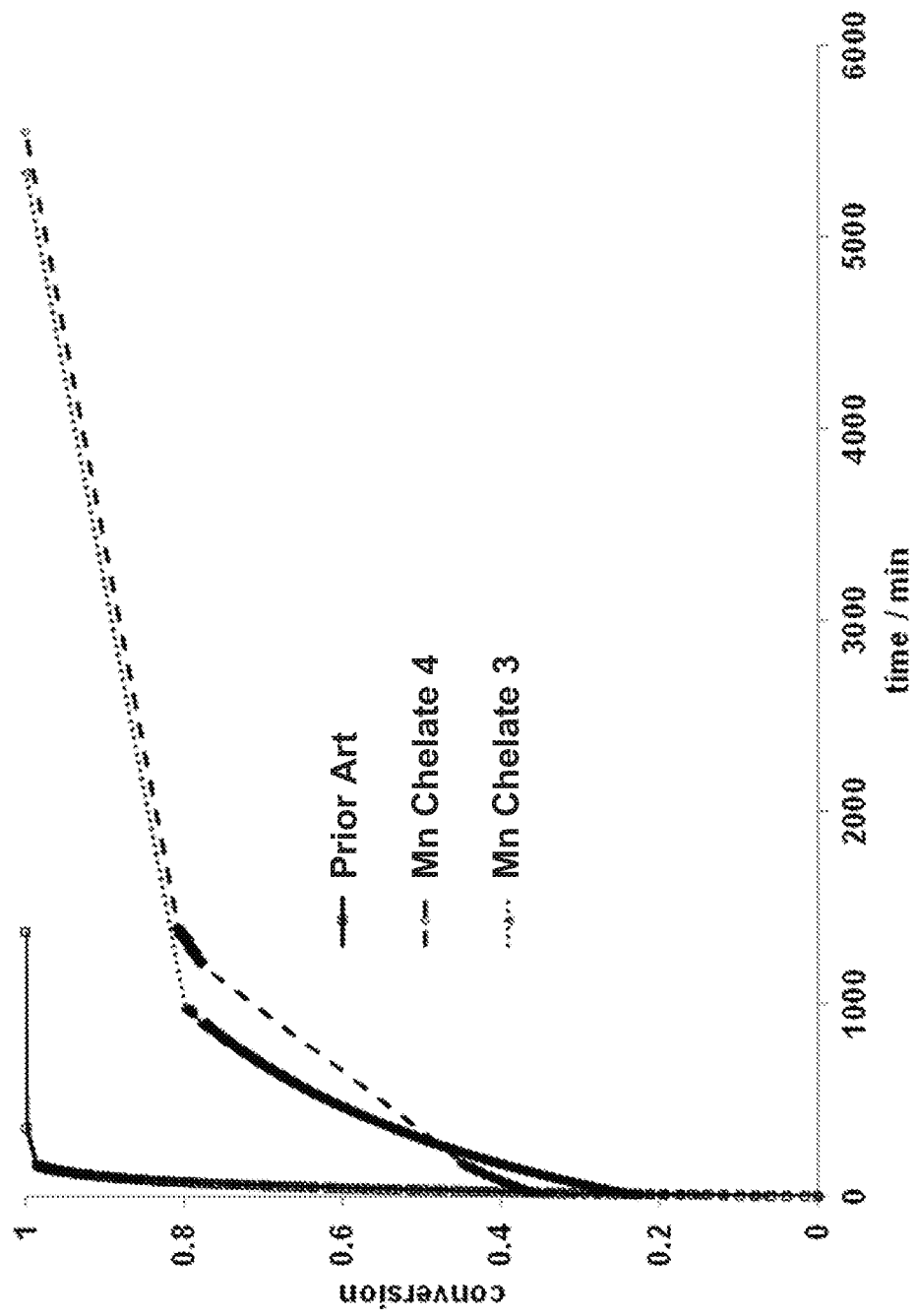

The direct comparison of the conversation calculated for any of the transmetallation experiments carried out with the prior art Mn Chelate, Mn Chelate 3 and Mn Chelate 4 (e.g., at different pH; different $Zn^{2+}$ or $Cu^{2+}$ concentration) demonstrated that the prior art Mn Chelate reaches a full conversion at much shorter time point than Mn Chelate 3, and the complex Mn Chelate 4 dissociates even slower. The conversion caused by competing $Cu^{2+}$ was calculated and displayed in FIGS. 9 and 10.

Figure 11:
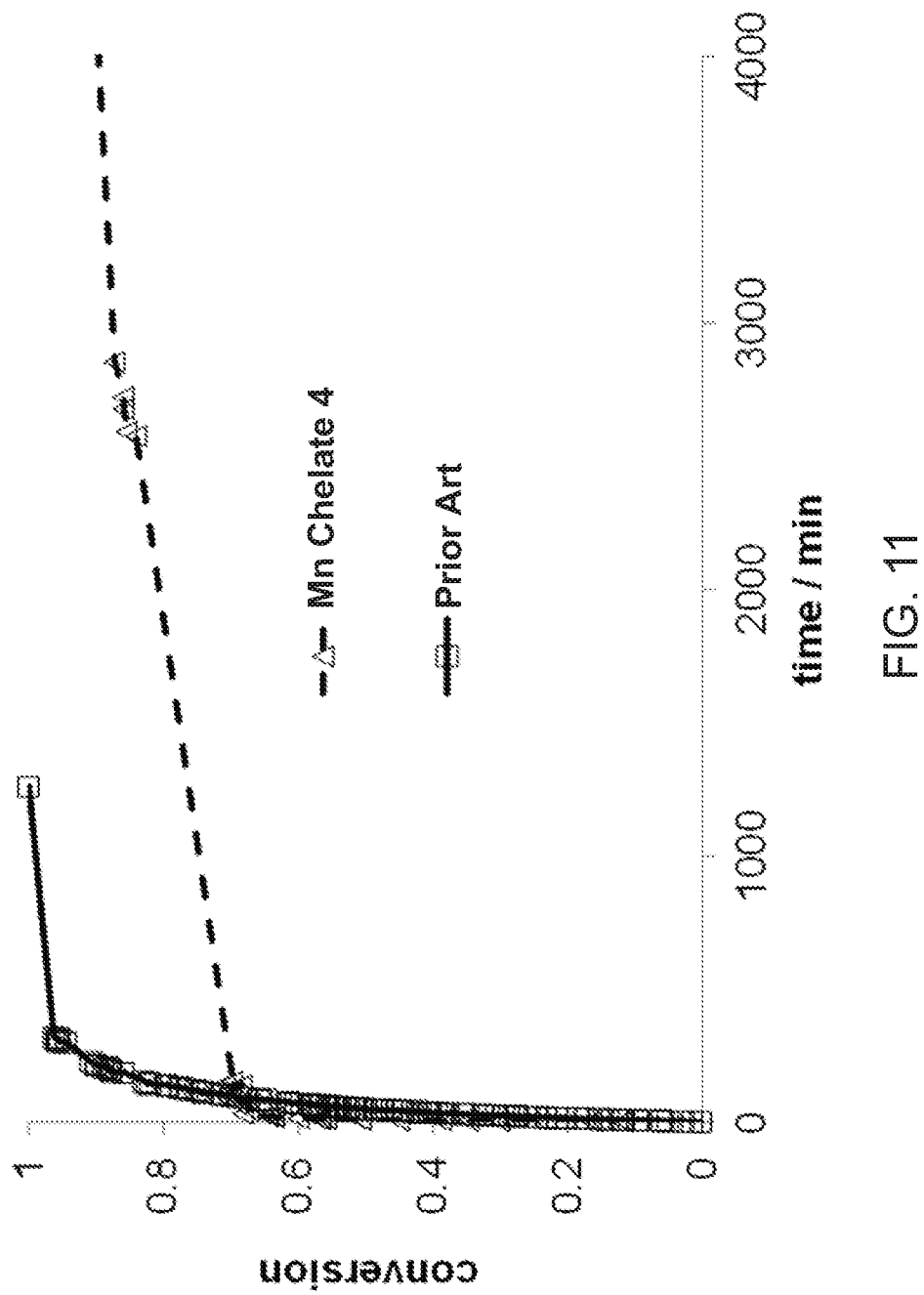
FIG. 11 illustrates the results obtained for a transmetallation reaction with $Zn^{2+}$ with a prior art Mn chelate compared with a compound of the invention.

With the same mathematical approach, the conversion caused by transmetallation reaction with $Zn^{2+}$ was also compared for the prior art Mn Chelate and Mn Chelate 4 (FIG. 11). This assessment clearly demonstrated the superior kinetic inertness of Mn Chelate 4 with respect to the prior art Mn Chelate.

Therefore, Mn Chelate 3 and Mn Chelate 4 demonstrated a different and slower dissociation mechanism in the $Cu^{2+}$ and $Zn^{2+}$ transmetallation with respect to the prior art Mn chelate. Surprisingly, an improved kinetic inertness was demonstrated by directly comparing the conversion of the three compounds occurred during the transmetallation reaction between the MnL (i.e., Mn(II) complex) and $Zn^{2+}$ or $Cu^{2+}$ under the same experimental conditions. All dissociation kinetics results showed an evident improvement in overall kinetic inertness for Mn Chelate 3 and Mn Chelate 4 with respect to the prior art Mn Chelate as reference. Indeed, Mn Chelate 4 resulted as the most kinetically inert compound examined in all experimental conditions. It is possible to hypothesize that the presence of side chains with —OH groups can wrap around the smaller Mn(II) metal successfully protecting the Mn from dissociation hence contributing to an increased kinetic inertness of this class of Mn(II) based chelates.

The invention claimed is:
1. A compound represented by:

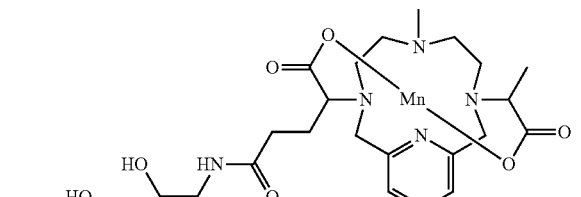

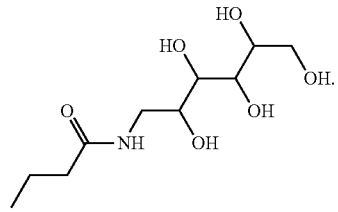

Mn Chelate 5 Racemate

2. A compound represented by:
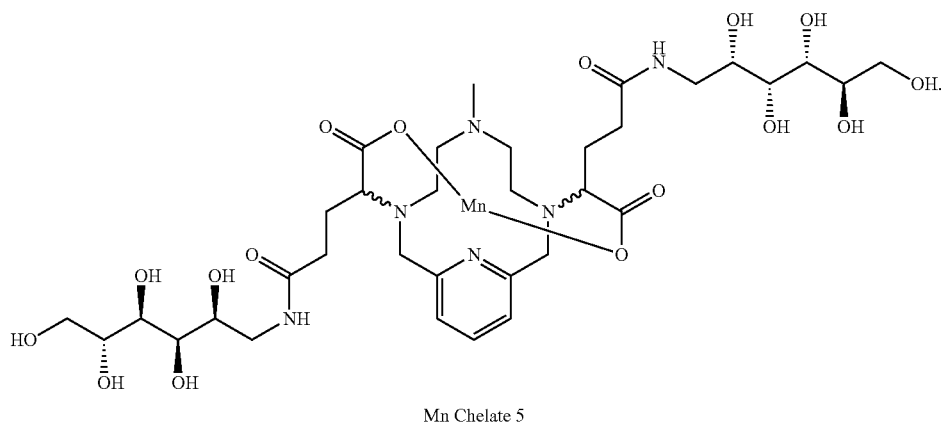
Mn Chelate 5
3. The compound of claim 2, which is diastereomerically pure.
4. A compound represented by:
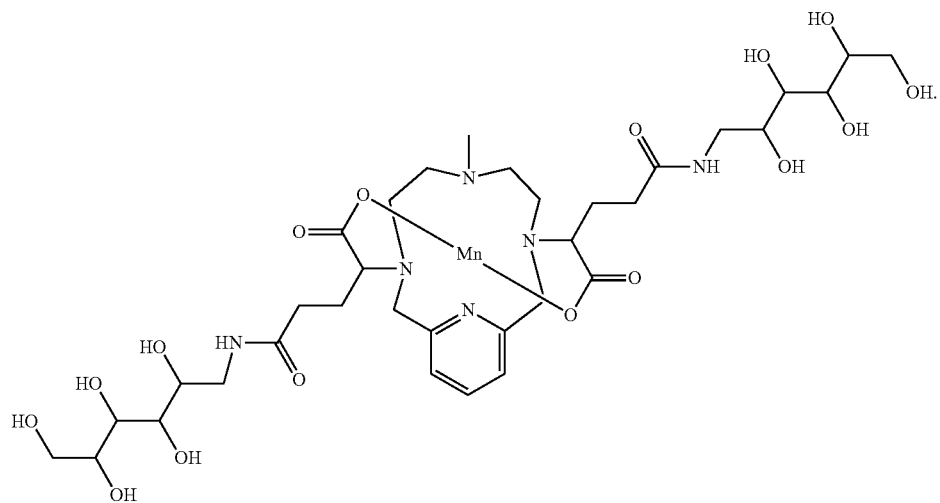
5. The compound of claim 4, which is diastereomerically pure.
6. The compound of claim 4, wherein said Mn is an enriched isotope of Mn selected from $^{52}$Mn or $^{54}$Mn.
* * * * *